(12) United States Patent
Ingalhalikar et al.

(10) Patent No.: US 9,402,656 B2
(45) Date of Patent: Aug. 2, 2016

(54) SPINOUS PROCESS FUSION DEVICES

(75) Inventors: Aditya Ingalhalikar, Bryn Mawr, PA (US); Jason Zappacosta, Philadelphia, PA (US); Michael Lee Boyer, II, Phoenixville, PA (US); David C. Paul, Phoenixville, PA (US); Daniel Laskowitz, Lancaster, PA (US); Jason Cianfrani, East Norriton, PA (US); Jody L. Seifert, Birdsboro, PA (US); William E. Duffield, Collegeville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 13/406,606

(22) Filed: Feb. 28, 2012

(65) Prior Publication Data

US 2012/0221050 A1  Aug. 30, 2012

Related U.S. Application Data

(63) Continuation-in-part of application No. 12/557,819, filed on Sep. 11, 2009, now Pat. No. 9,179,944.

(51) Int. Cl.
 *A61B 17/70* (2006.01)

(52) U.S. Cl.
 CPC ......... *A61B 17/7065* (2013.01); *A61B 17/7068* (2013.01)

(58) Field of Classification Search
 CPC .............. A61F 2/4405; A61B 17/7062; A61B 17/7067; A61B 17/7068
 USPC ..................... 623/17.11–17.16; 606/246–279
 See application file for complete search history.

(56) References Cited

U.S. PATENT DOCUMENTS

| | | | | |
|---|---|---|---|---|
| 3,056,852 | A * | 10/1962 | Sachs ........................ | 174/153 G |
| 7,993,374 | B2 * | 8/2011 | Zucherman et al. ......... | 606/249 |
| 8,105,358 | B2 * | 1/2012 | Phan ............................ | 606/249 |
| 8,128,659 | B2 * | 3/2012 | Ginsberg et al. ............ | 606/246 |
| 8,206,420 | B2 * | 6/2012 | Patel et al. ................... | 606/249 |
| 2002/0091446 | A1 | 7/2002 | Zucherman et al. | |
| 2003/0040746 | A1 * | 2/2003 | Mitchell et al. ................ | 606/61 |
| 2003/0216736 | A1 * | 11/2003 | Robinson et al. .............. | 606/61 |
| 2005/0228376 | A1 | 10/2005 | Boomer | |
| 2006/0229611 | A1 | 10/2006 | Avery | |
| 2006/0247640 | A1 * | 11/2006 | Blackwell et al. .............. | 606/71 |
| 2008/0183211 | A1 * | 7/2008 | Lamborne et al. ............ | 606/249 |
| 2008/0183218 | A1 * | 7/2008 | Mueller et al. ................ | 606/280 |
| 2008/0281359 | A1 * | 11/2008 | Abdou ........................... | 606/246 |
| 2010/0036419 | A1 * | 2/2010 | Patel et al. .................... | 606/249 |
| 2010/0087860 | A1 * | 4/2010 | Chin et al. .................... | 606/249 |
| 2010/0211101 | A1 * | 8/2010 | Blackwell et al. ............ | 606/246 |
| 2010/0318127 | A1 * | 12/2010 | Phan et al. .................... | 606/249 |
| 2011/0022090 | A1 * | 1/2011 | Gordon et al. ................ | 606/249 |
| 2011/0066186 | A1 * | 3/2011 | Boyer et al. .................. | 606/249 |
| 2011/0087285 | A1 * | 4/2011 | Khajavi et al. ................ | 606/248 |

(Continued)

FOREIGN PATENT DOCUMENTS

WO  2005122922 A2  12/2005
WO  2011031924 A2  3/2011

*Primary Examiner* — Eduardo C Robert
*Assistant Examiner* — Michelle C Eckman

(57) ABSTRACT

The present disclosure generally relates to a device for positioning and immobilizing at least two adjacent vertebrae. In particular, in one or more embodiments, the present disclosure relates to spinous process fusion devices that distract and immobilize the spinous processes of adjacent vertebrae.

20 Claims, 25 Drawing Sheets

(56) References Cited

U.S. PATENT DOCUMENTS

| | | |
|---|---|---|
| 2011/0144692 A1* | 6/2011 | Saladin et al. ............... 606/249 |
| 2011/0184468 A1 | 7/2011 | Metcalf, Jr. et al. |
| 2011/0224731 A1* | 9/2011 | Smisson et al. ............... 606/249 |
| 2011/0319936 A1* | 12/2011 | Gordon et al. ............... 606/248 |
| 2012/0016418 A1* | 1/2012 | Chin et al. ............... 606/249 |
| 2012/0089184 A1* | 4/2012 | Yeh ............... 606/248 |
| 2012/0089187 A1* | 4/2012 | Forton ............... A61B 17/1655 606/250 |
| 2012/0101528 A1* | 4/2012 | Souza et al. ............... 606/249 |
| 2012/0109198 A1* | 5/2012 | Dryer et al. ............... 606/248 |
| 2012/0109203 A1* | 5/2012 | Dryer et al. ............... 606/249 |
| 2012/0136390 A1* | 5/2012 | Butler ............... A61B 17/7067 606/248 |
| 2012/0136393 A1* | 5/2012 | Auyoung ............... 606/249 |
| 2012/0143252 A1* | 6/2012 | Robinson ............... 606/248 |
| 2012/0150228 A1* | 6/2012 | Zappacosta et al. ............... 606/248 |
| 2012/0158061 A1* | 6/2012 | Koch et al. ............... 606/248 |
| 2012/0191135 A1* | 7/2012 | Abdou ............... 606/248 |

\* cited by examiner

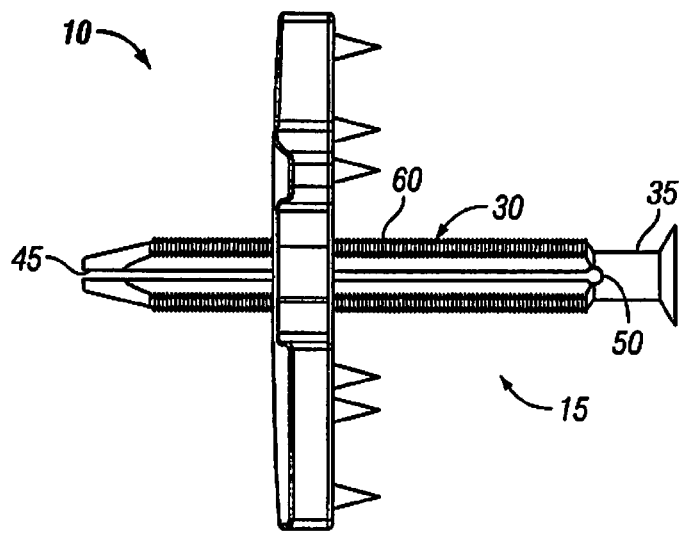
FIG. 3
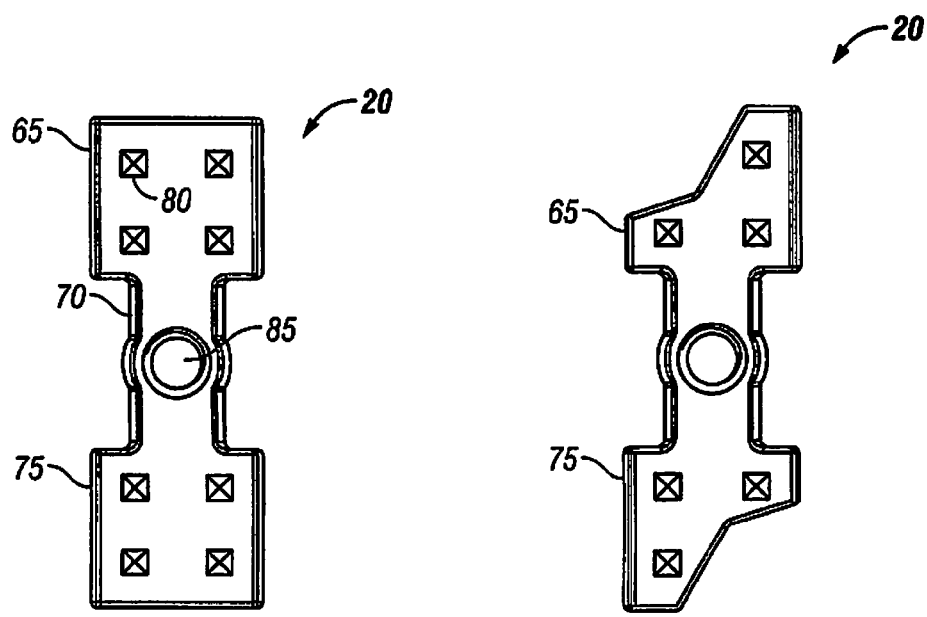
FIG. 4  FIG. 5

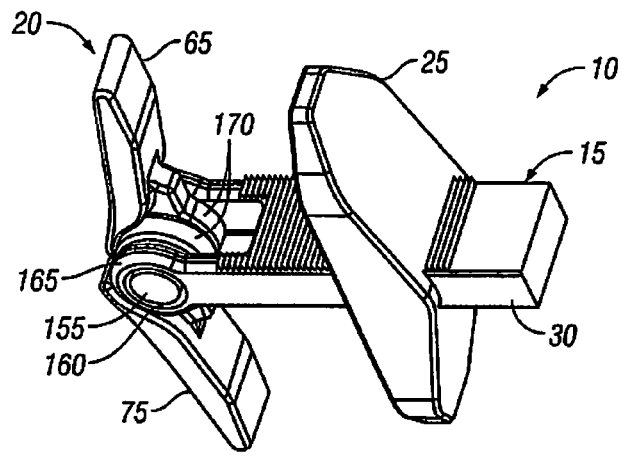
*FIG. 12*
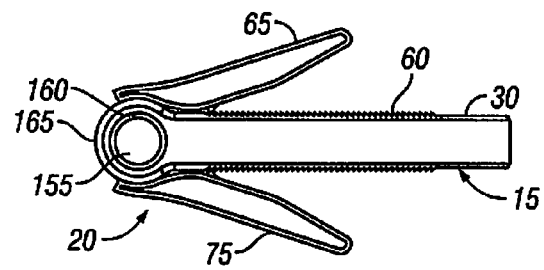 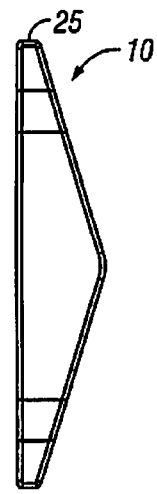
*FIG. 13*
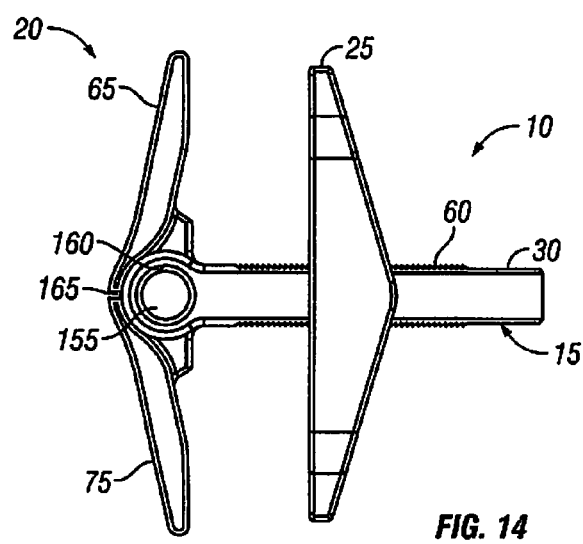
*FIG. 14*

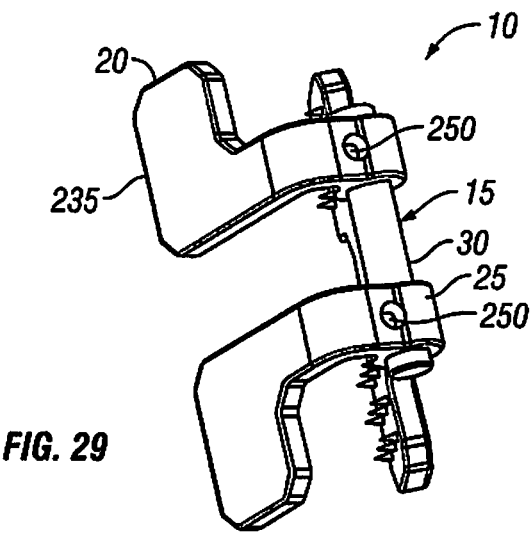
FIG. 29
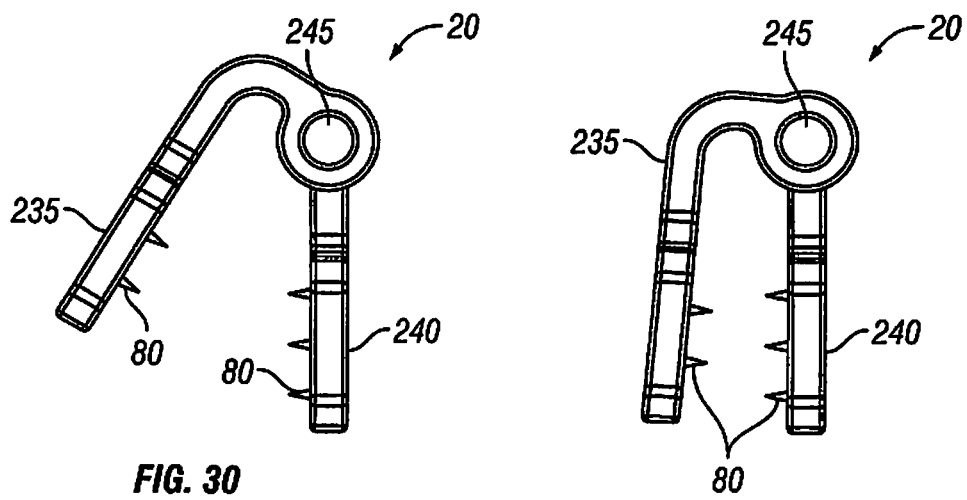
FIG. 30
FIG. 31

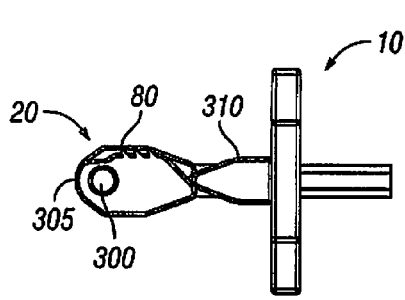
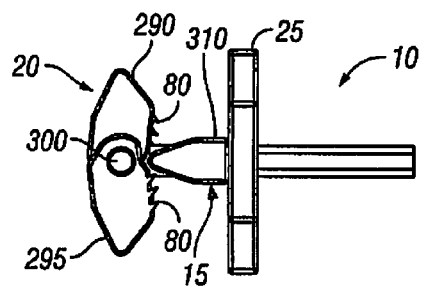
FIG. 35  FIG. 36
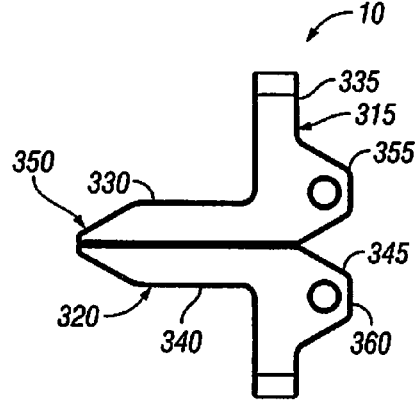
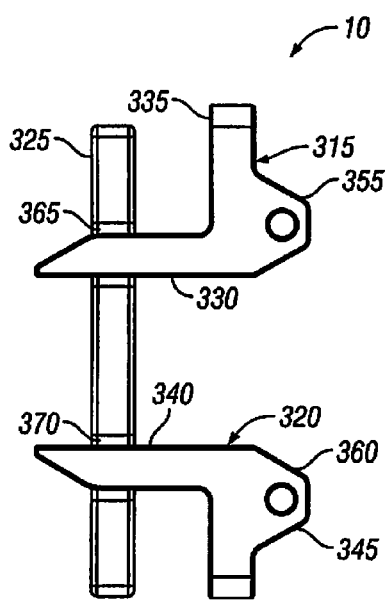
FIG. 37  FIG. 38

SPINOUS PROCESS FUSION DEVICES

CROSS REFERENCE TO RELATED APPLICATIONS

This Patent Application is a continuation-in-part application claiming priority to U.S. patent application Ser. No. 12/557,819, filed on Sep. 11, 2009, now U.S. Pat. No. 9,179,944, the entire content of which is incorporated by reference.

FIELD OF THE INVENTION

The present disclosure generally relates to a device for positioning and immobilizing at least two adjacent vertebrae. In particular, in one or more embodiments, the present disclosure relates to spinous process fusion devices that distract and/or immobilize the spinous processes of adjacent vertebrae.

BACKGROUND

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

Typically, weaknesses in the spine are corrected by using devices that fuse one or more vertebrae together. Common devices involve plate systems that align and maintain adjacent vertebrae in a desired position, with desired spacing. These devices, commonly referred to as bone fixation plating systems, typically include one or more plates and screws for aligning and holding vertebrae in a fixed position with respect to one another. When implanting these devices in a patient, it may be desirable for interspinous distraction, for example, to obtain a desired spacing between the fused spinous processes.

Thus, there is a need for a device that provides structural stability to adjacent vertebrae, for example, a plate system that can distract and/or immobilize the spinous processes of adjacent vertebrae.

SUMMARY OF THE INVENTION

Various systems, devices and methods related to a spinous process fusion device are provided. In some embodiments, an implantable device comprises a body comprising a rod member; a first wing operatively attached to the body, the first wing comprising a substantially straight portion that transitions into a substantially curved portion; and a second wing operatively attached to the body, the second wing comprising a substantially straight portion that transitions into a substantially curved portion.

In some embodiments, an implantable device comprises a body; a first wing operatively attached to the body, the first wing comprising a substantially curved portion including a first set of teeth; and a second wing operatively attached to the body, the second wing comprising a substantially curved portion including a second set of teeth.

In some embodiments, an implantable device comprises a body comprising a central barrel; a first wing operably attached to the body, the first wing comprising a substantially straight portion that transitions into a substantially curved portion; and a second wing operably attached to the body, the second wing comprising a substantially straight portion that transitions into a substantially curved portion.

BRIEF DESCRIPTION OF THE DRAWINGS

FIG. 3 is a lateral view of one embodiment of the spinous process fusion device of the present invention with one of the wings removed.

FIG. 4 is a view of one embodiment of a wing for use with an embodiment of a spinous process fusion device of the present invention.

FIG. 5 is a view of another embodiment of a wing for use with an embodiment of a spinous process fusion device of the present invention.

FIG. 12 is a perspective view of another embodiment of a spinous process fusion device of the present invention having a ratcheting lock and an expandable wing.

FIG. 13 is a lateral view of an embodiment of the spinous process fusion device of FIG. 12 with the expandable wing in a folded position.

FIG. 14 is a lateral view of an embodiment of the spinous process fusion device of FIG. 12 with the expandable wing in an upright position.

FIG. 29 is a perspective view of another embodiment of a spinous process fusion device of the present invention having clampable wings.

FIG. 30 is a lateral view of an embodiment of the spinous process fusion device of FIG. 29 with the clampable wings in an open position.

FIG. 31 is a lateral view of an embodiment of the spinous process fusion device of FIG. 29 with the clampable wings in a closed position.

FIGS. 35-36 are lateral view of an embodiment of a spinous process fusion device of the present invention having expandable wings.

FIGS. 37-38 are lateral views of an embodiment of a spinous process fusion device of the present invention having distraction elements.

DETAILED DESCRIPTION OF THE ILLUSTRATED EMBODIMENTS

The present disclosure generally relates to a device for positioning and immobilizing at least two adjacent vertebrae. In particular, in one or more embodiments, the present disclosure relates to spinous process fusion devices that distract and/or immobilize the spinous processes of adjacent vertebrae. The fusion devices may be implanted in a patient, for example, without the need for removal of the supraspinous ligament. In certain embodiments, the fusion devices provide for distraction of the interspinous space, for example, allowing use of the device as a spacer and a clamp.

Figure 1:
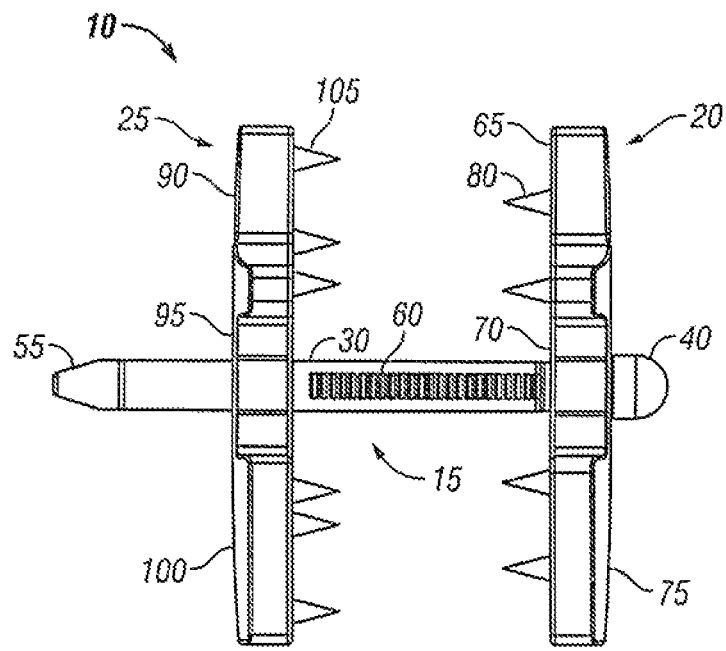
FIG. 1 is a lateral view of one embodiment of a spinous process fusion device of the present invention having a ratcheting lock.
Figure 2:
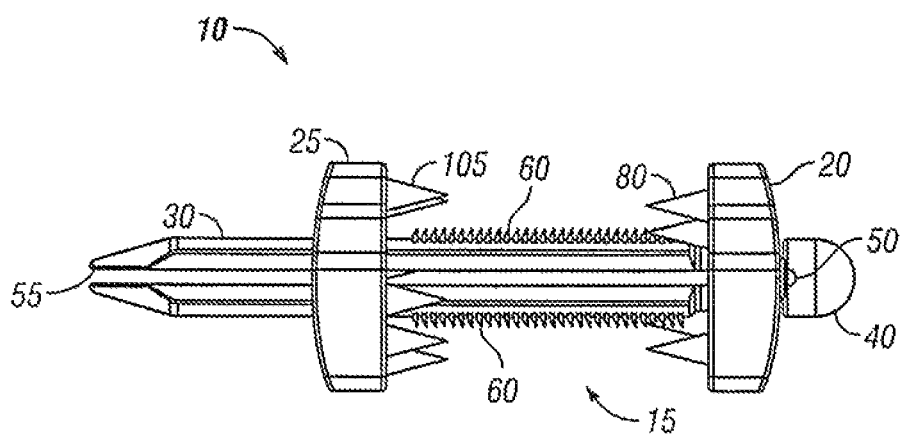
FIG. 2 is a top view of an embodiment of the spinous process fusion device of FIG. 1.

FIGS. 1-2 illustrate a spinous process fusion device 10 in accordance with embodiments of the present invention. As illustrated, the spinous process fusion device 10 may comprise a body 15, a first wing 20 coupled to the body, and a second wing 25. In accordance with embodiments of the present invention, the second wing 25 may be secured to the body 15 by a ratcheting lock. When installed in a patient, the first wing 20 and the second wing 25 may engage spinous processes of adjacent vertebra above and below the interspinous space. The device 10 should thus, for example, immobilize the lumbar motion segment associated with the vertebrae of the engaged spinous processes. In certain embodiments, the device 10 should immobilize the lumbar motion segment without the need for additional devices.

An embodiment of the body 15 will be described with reference to FIGS. 1-3. It should be understood that the first wing 20 is not illustrated on FIG. 3 to more particularly illustrate certain details of the body 15. The body 15 may have a length, for example, of about 20 millimeters to about 50 millimeters. As illustrated, the body 15 may comprise a rod 30, a connector portion 35, and head 40. The connector portion 35 connects the rod 30 and the head 40. The rod 30 generally may be configured so that it can spread to increase the diameter of the rod 30. In the illustrated embodiment, the rod 30 has an opening 45 extending there through in the direction of the longitudinal axis. In certain embodiments, the rod 30 may be configured so that insertion of a pin 50 or screw into the opening 45 spreads the rod 30. As such, the diameter of the rod 30 may be increased. The rod 30 further includes a tapered end 55 opposite the head 40.

The rod 30 further may include a series of ratchet receivers that comprise protuberances 60. The protuberances 60 may be, for example, in the shape of an inclined wedge with the inclined portion of the protuberance extending in the direction of the tapered end 55 of the rod 30. As illustrated, the protuberances 60 may be arranged along the longitudinal axis of the rod 30. The protuberances 60 further may be arranged on a first and a second side of the rod 30. In the illustrated embodiment, the protuberances 60 are integrally formed with the rod 30.

An embodiment of the first wing 20 will be described in more detail with respect to FIGS. 1-2 and 4. The first wing 20 may extend transversely from the body 15 and be disposed over the connecting portion 35 of the body 15 between the rod 30 and the head 40. The first wing 20 may have a length sufficient to span, for example between adjacent spinous processes, such as about 20 millimeters to about 60 millimeters. The first wing 20 may comprise an upper portion 65, a central portion 70, a lower portion 75, and teeth 80. The upper portion 65 and the lower portion 75 may have widths respectively of about 10 millimeters to about 80 millimeters, while the central portion 70 may have a width of about 5 millimeters to about 10 millimeters. In the illustrated embodiment, the upper portion 65 and the lower portion 75 are each generally rectangular in shape. It should be understood that other shapes for these portions of the first wing 20 may also be suitable. By way of example, the wing may be rectangular with rounded corners, oval, circular, football shaped, wedge-shaped, and a variety of other shapes suitable for a particular application.

An alternative embodiment of the first wing 20 is illustrated in FIG. 5. As illustrated in FIG. 5, each of the upper portion 65 and the lower portion 75 may have a cutout, for example, to facilitate stacking of more than one spinous process fusion device 10. The cutout may be configured so that the upper portion 65 and the lower portion 75 of the first wing 20 mate. In this manner, an upper portion 65 of one spinous process fusion device 10 may engage the same spinous process as the lower portion 75 of another fusion device 10. While not illustrated, the first wing 20 may be configured to angulate on the connector portion 35, for example, to conform to the patient's anatomy. By way of example, the first wing 20 may be configured to rotate about its longitudinal axis.

Referring again to FIGS. 1-2 and 4, the central portion 70 of the first wing may have an opening 85 that should allow the first wing 20 to be placed onto the connecting portion 35. The opening 85 should be configured so that the first wing 20 cannot be removed from the connecting portion 35 over the rod 30. The first wing 20 may include the teeth 80 (e.g., spikes) for engaging the spinous processes. By way of example, the teeth 80 may bite into the spinous processes clamping the spinous processes in position. As illustrated, the teeth 80 extend from the side of the first wing 20 that is facing the second wing 25.

Second wing 25 may be placed onto the rod 30 over the protuberances 60, in accordance with embodiments of the present invention. Second wing may extend transversely from the body 15. The second wing 25 may have a length sufficient to span, for example between adjacent spinous processes, such as about 20 millimeters to about 60 millimeters. As illustrated, the second wing 25 may comprise upper portion 90, central portion 95 and lower portion 100. The upper portion 90 and lower portion 100 may have widths respectively of about 10 millimeters to about 20 millimeters, while the central portion 95 may have a width of about 5 millimeters to about 10 millimeters. As described above with respect to the first wing 20, the upper portion 90 and the lower portion 100 of the second wing 25 may also be rectangular shaped or any other shape suitable for a particular application. In addition, to facilitate stacking, the upper portion 90 and the lower portion 100 may also have cutouts, in certain embodiments. The second wing 25 further may include teeth 105 (e.g., spikes) for engaging the spinous processes. The teeth 105 may, for example, bite into the spinous process clamping them in position. In the illustrated embodiment, the teeth 105 may extend from the side of the second wing 25 that is facing the first wing 20.

Figure 6:
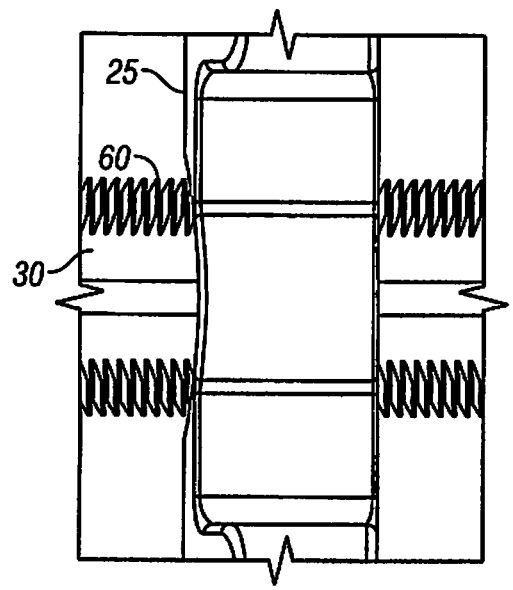
FIG. 6 is a view of one embodiment of a ratcheting lock for use with an embodiment of a spinous process fusion device of the present invention.
Figure 7:
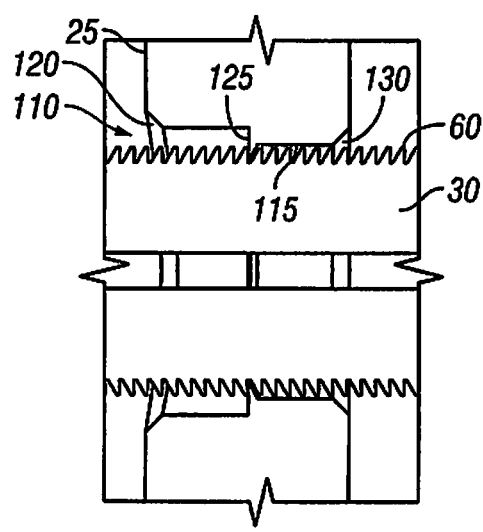
FIG. 7 is a cross-sectional view of the ratcheting lock of FIG. 6.

Referring now to FIGS. 6-7, the second wing 25 further may include an opening 110 that should allow the second wing 25 to be placed onto the rod 30. The interior wall 115 of the second wing 25 surrounding the opening 100 may include ratcheting members 120, 125, 130 that extend outwardly from the interior wall 115. A first ratcheting member 120 may extend from the interior wall 115 at one edge of the opening 110. The first ratcheting member 120 may be grooved so that it fits over a corresponding one of the protuberances 60. A second ratcheting member 125 may extend from the interior wall 115 in the central area of the interior wall 115. The second ratcheting member 125 may be in the shape of an inclined wedge with the inclined portion in the opposite direction of the inclined portion of the protuberances 60 so that the second ratcheting member 125 fits into a space between adjacent protuberances 60. The third ratcheting member 130 may extend from the interior wall 115 at the opposite edge of the opening 110 from the first ratcheting member 120. The third ratcheting member 130 may also be grooved so that it fits over a corresponding one of the protuberances 60.

When the second wing 25 is placed over the rod 30, the ratcheting members 120, 125, 130 should interact with the protuberances 60 to create a one-way ratcheting lock, in accordance with embodiments of the present invention. By way of example, the ratcheting members 120, 125, 130 and the protuberances 60 should be configured so that, as the second wing 25 is slid onto the rod 30, the second wing 25 is movable over the protuberances 60. Once the second wing 25 is slid onto the rod 30, the pin 50 may be slid into the opening 45, thereby spreading the rod 30. In this manner, the ratcheting members 120, 125, 130 should engage the protuberances 60 and prevent movement when the second wing 25 is urged in the opposite direction, for example, when removal of the second wing 25 from the rod 30 is attempted. The second wing 25, thus, may be ratcheted onto the rod 30. While the one-way ratcheting lock is described with respect to the illustrated embodiment, it should be understood that other techniques may be used for the one-way ratcheting lock in accordance with embodiments of the present invention. In addition, while FIGS. 6-7 illustrate pin 50 used to spread the rod 30 so that the ratcheting members 120, 125, 130 engage the protuberances 50, securing the second wing 25 on the rod 30, other suitable techniques may be used to ratchet the second wing 25 onto the rod 30. By way of example, a cam may be used for expanding the rod 30 to engage the ratcheting members 120, 125, 130 with the protuberances 60. Alternatively, the ratcheting members 120, 125, 130 may be hinged to allow movement over the protuberances 60 in one direction, but not movement in the opposite direction.

Figure 8:
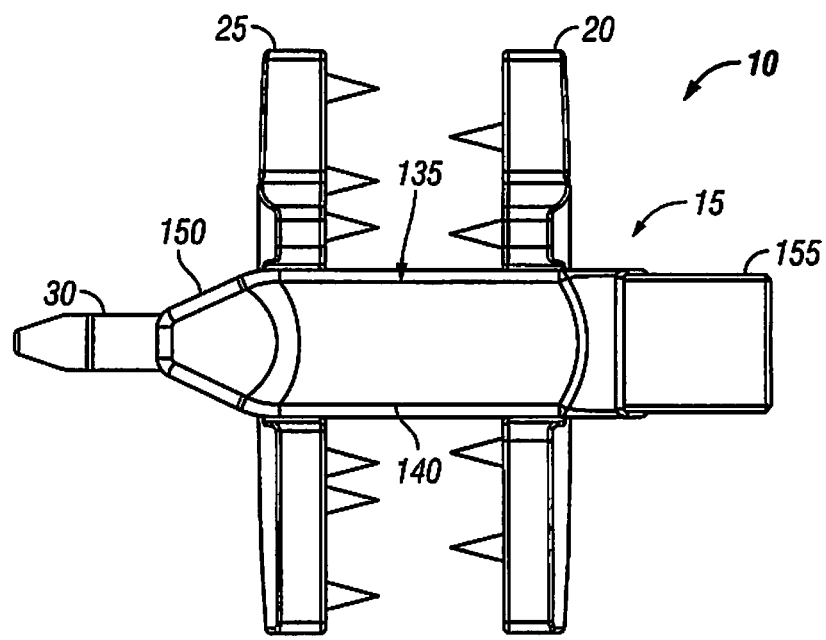
FIG. 8 is a lateral view of another embodiment of a spinous process fusion device of the present invention having a ratcheting lock and a central barrel.
Figure 9:
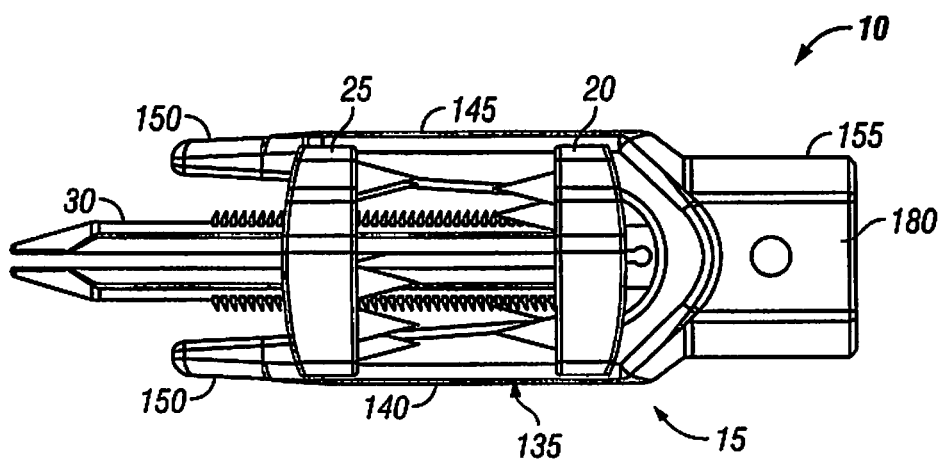
FIG. 9 is a top view of an embodiment of the spinous process fusion device of FIG. 8.

Referring now to FIGS. 8-9, the spinous process fusion device 10 further comprising a central barrel 135 is illustrated in accordance with another embodiment of the present invention. As illustrated, spinous process fusion device 10 comprises the body 15, the first wing 20, and the second wing 25. In the illustrated embodiment, the body 15 further may comprise central barrel 135. Central barrel 135 may comprise first side 140 and second side 145, which each extend on either side of the rod 30. The first side 140 and the second side 145 may have widths respectively of about 10 millimeters to about 30 millimeters. Each of the first side 140 and the second side 145 may include a tapered end 150. The tapered end 150 should facilitate insertion of the spinous process fusion device 10 into the interspinous space between adjacent vertebrae. Moreover, the width of the first side 140 and the second side 145 generally should provide for distraction of the interspinous space during placement of the device 10. Thus, the device 10 may function, for example, as both a spacer and a clamp. Moreover, the first side 140 and the second side 145 generally should restrict and/or prevent rotation of the first wing 20 and the second wing 25 about the connecting portion 35 and the rod 30, respectively. As illustrated in FIG. 4, the central portion 70 of the first wing 20 may have a narrower width than the upper portion 65 and lower portion 75 thereof so that the upper portion 65 and the lower portion 75 may extend over the first side 140 and the second side 145 of the central barrel 135. Likewise, the central portion 95 of the second wing 25 may also have a narrower width than the upper portion 90 and the lower portion 100 thereof. As such, the central barrel 135 may act as a guide for the second wing 25 when it is inserted onto the rod 30 so that it is in alignment with the first wing 20. The central barrel 135 further may comprise an end 155 that connects the first side 140 and the second side 145. The end 155 may comprise an opening 160 through which the pin (not illustrated) may be inserted, in certain embodiments.

As previously mentioned, the spinous process fusion device 10 may be implanted in a patient to, for example, immobilize the spinous processes of adjacent vertebrae. An embodiment of implanting the spinous process fusion device 10 in a patient may comprise inserting a spinous fusion device 10 comprising a body 15 and a first wing 20 between adjacent spinous processes of a patient. The spinous fusion device 10 generally may be inserted until the teeth 80 of the first wing 20 engage the adjacent spinous processes both above and below the interspinous space. In certain embodiments, the second wing 25 generally may not be on the device 10 when it is inserted. If used, the central barrel 135 may provide for distraction of the interspinous space during placement of the device 10. However, it should be understood that additional techniques and/or devices may be used for distraction of the interspinous space. In addition, the design of the spinous process fusion device 10 generally should allow its insertion between adjacent spinous processes without removal of the supraspinous ligament. Once the spinous fusion process device 10 has been placed between the adjacent spinous processes, the second wing 25 may be placed onto the rod 30 such that the teeth 105 of the second wing 25 engage the adjacent spinous processes both above and below the interspinous space. The second wing 25 generally may be positioned on the rod 30 such that the first wing 20 and the second wing 25 clamp the spinous processes in place. Once the second wing 25 is positioned in the desired location, the pin 50 may be placed into opening 45 of the rod 30 to expand the rod 30, engaging the ratcheting members 120, 125, 130 with the protuberances 60. The one-way ratcheting lock from interaction of the protuberances 60 of the rod 30 and the ratcheting members 120, 125, 130 of the second wing 25 generally should prevent removal of the second wing 25. In this manner, the lumbar motion segment may be immobilized, for example, without the need for additional devices.

Figure 10:
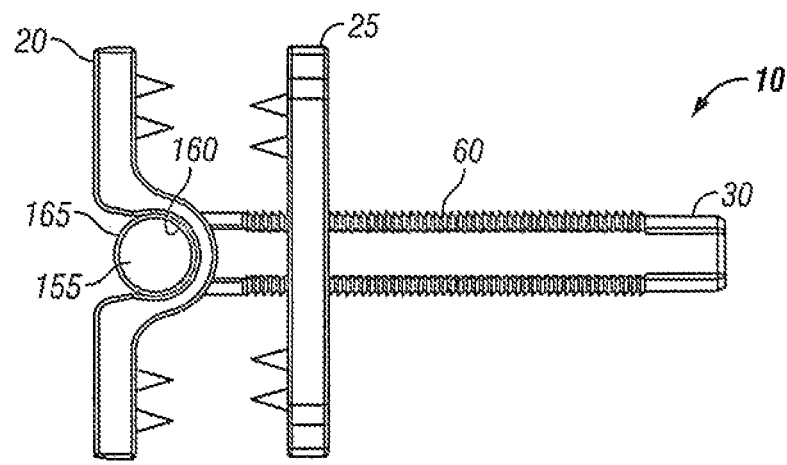
FIG. 10 is a lateral view of another embodiment of a spinous process fusion device of the present invention having a ratcheting lock and a pivoting wing.
Figure 11:
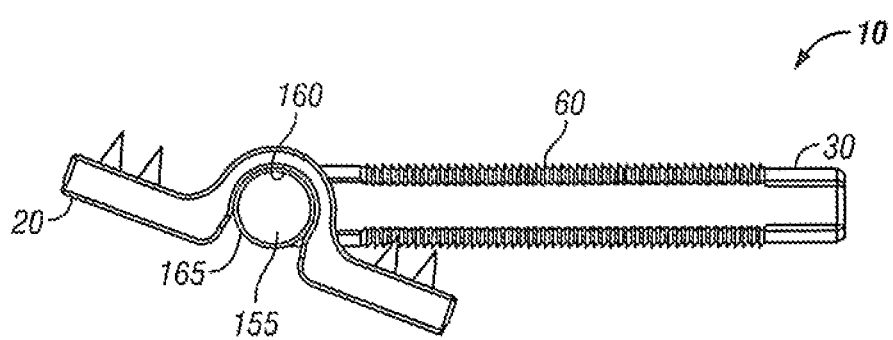
FIG. 11 is a lateral view of one embodiment of the spinous process fusion device of FIG. 10 with one of the wings removed.

FIGS. 10-11 illustrate an embodiment of the spinous process fusion device 10 having a rotating wing. As illustrated, the first wing 20 may be rotatably connected to the body 15, in accordance with embodiments of the present invention. Rotating of the first wing 20 about its central axis may allow the device 10, for example, to better conform to the patient's anatomy. In the illustrated embodiment, the first wing 20 is rotatably connected to the body 15 at pin 155. The central portion 70 of the first wing 20 may be generally curved for fitting around a portion of the pin 155. The pin 155 may fit through a corresponding opening 160 in a rounded end 165 of rod 30. Pin 155 may be tightened, for example, to lock the first wing 20 in a desired position. In operation, the second wing 25 may be placed onto the device 10 so that the first wing 20 and the second wing 25 may clamp adjacent spinous processes in place. As previously discussed, the device 10 may include a one-way ratcheting lock, in which the interaction of the protuberances 60 with the second wing 25 should prevent removal of the second wing 25. While not illustrated, the central barrel 135 may be used, for example, to provide for interspinous distraction.

FIGS. 12-14 illustrate an embodiment of the spinous process fusion device 10 having an expandable wing. As illustrated, the first wing 20 may be expandable, in accordance with embodiments of the present invention. By way of example, each of the upper portion 65 and the lower portion 75 of the first wing 20 may be pivotably connected to the body 15 at pin 155. The upper portion 65 and lower portion 75 may each have a generally rounded end 170 for fitting around the pin 155. The pin 155 may fit through a corresponding opening 160 in a rounded end 165 of rod 30. The upper portion 65 and the lower portion 75 may each pivot at the pin 155 from a folded position (FIG. 13) to an upright position (FIG. 14). Pin 155 may be tightened, for example, to lock the first wing 20 in a desired position. While not illustrated, teeth generally may be present on the first wing 20 and/or the second wing 25 for engaging the spinous processes. In operation, the first wing 20 generally may expand, for example, as the device 10 is inserted into the interspinous space between adjacent spinous processes. Once the device 10 is positioned as desired, the second wing 25 may be placed onto the device 10 so that the first wing 20 and the second wing 25 may clamp adjacent spinous processes in place. As previously discussed, the device 10 may include a one-way ratcheting lock, in which the interaction of the protuberances 60 with the second wing 25 should prevent removal of the second wing 25. Alternatively, a set screw (not shown) may be used to lock the second wing 25 on the device 10. While not illustrated, the central barrel 135 may be used, for example, to provide for interspinous distraction.

Figure 15:
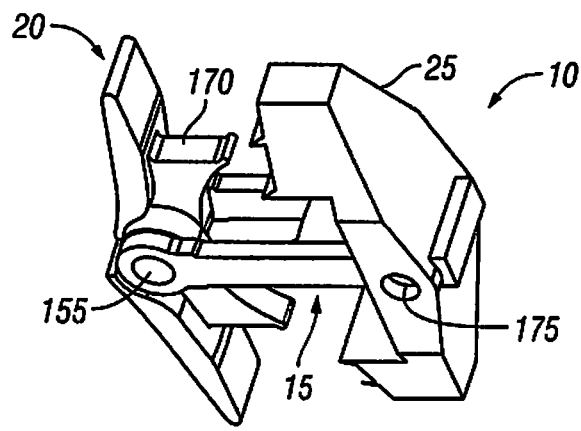
FIG. 15 is a perspective view of another embodiment of a spinous process fusion device of the present invention having an expandable wing with a flange.
Figure 16:
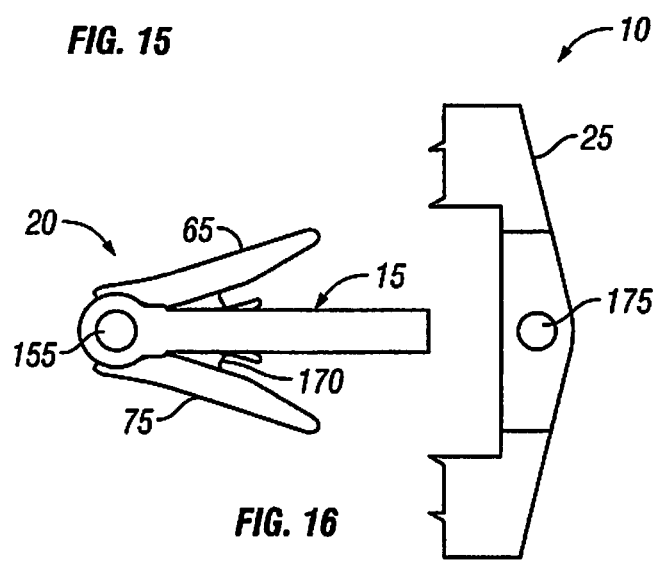
FIG. 16 is a lateral view of an embodiment of the spinous process fusion device of FIG. 15 with the expandable wing in a folded position.
Figure 17:
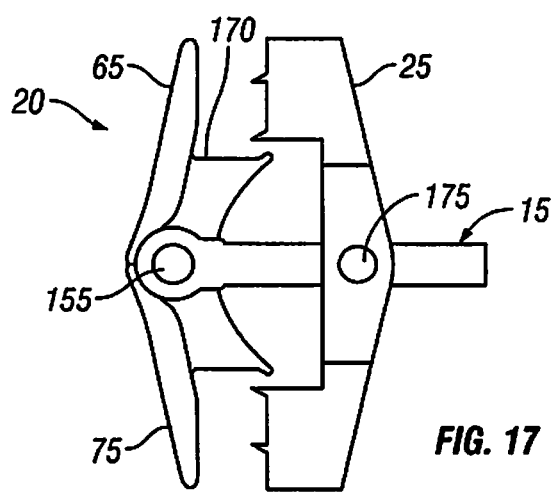
FIG. 17 is a lateral view of an embodiment of the spinous process fusion device of FIG. 15 with the expandable wing in an upright position and the flange extended.

FIGS. 15-17 illustrate another embodiment of the spinous process fusion device 10 having an expandable wing. As illustrated, the first wing 20 may further include an expandable flange 170 on the side facing the second wing 25, in accordance with embodiments of the present invention. The expandable flange 170 generally may provide for distraction of the interspinous space. In the illustrated embodiment, the first wing 20 is expandable. For example, the upper portion 65 and the lower portion 75 of the first wing 20 may each be pivotably connected at pin 155. The upper portion 65 and the lower portion 75 each may pivot at the pin 155 from a folded position (FIG. 16) to an upright position (FIG. 17). In the upright position, the expandable flange 170 generally should extend from the first wing 20 along the body 15. Pin 155 may be tightened, for example, to lock the first wing 20 and thereby the expandable flange 170 in a desired position. While not illustrated, teeth generally may be present on the first wing 20 for engaging the spinous processes. In operation, the first wing 20 generally may expand, for example, as the device 10 is inserted into the interspinous space between adjacent spinous processes. When the first wing 20 expands, the expandable flange 170 should extend from the first wing 20 thereby providing interspinous distraction. Once the device 10 is positioned as desired, the second wing 25 may be placed onto the device 10 so that the first wing 20 and the second wing 25 may clamp adjacent spinous processes in place. A set screw (not shown) may be inserted into opening 175 in the second wing 25 to lock the second wing 25 on the device 10. In an alternative embodiment, the device 10 may include a one-way ratcheting lock, in which the interaction of protuberances (not illustrated) with the second wing 25 should prevent removal of the second wing 25.

Figure 18:
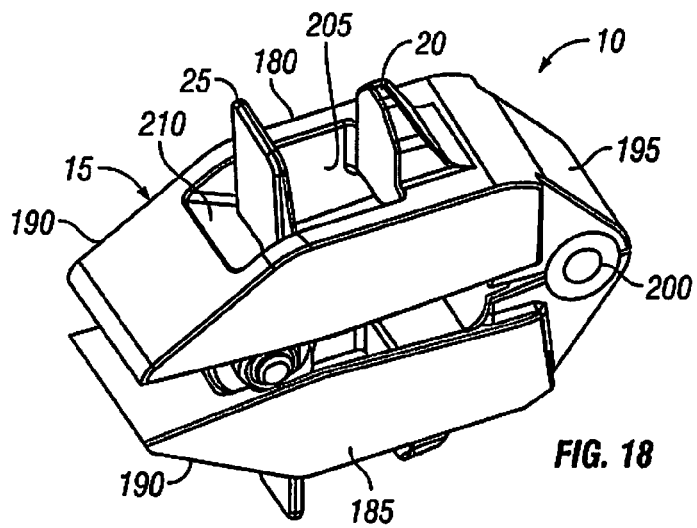
FIG. 18 is a perspective view of another embodiment of a spinous process fusion device of the present invention having an expandable wing.
Figure 19:
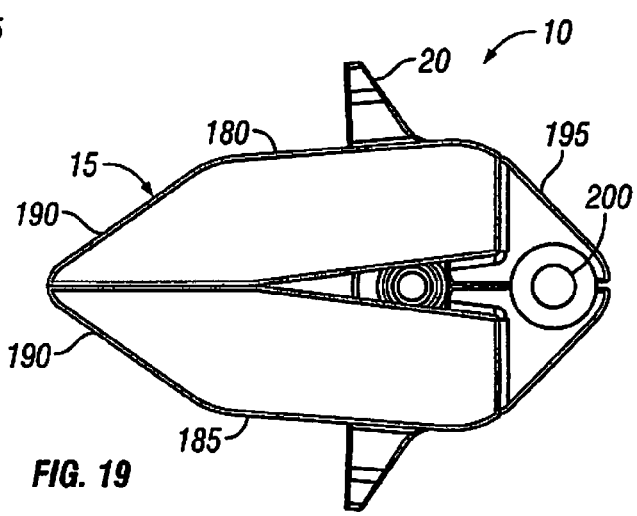
FIG. 19 is a lateral view of an embodiment of the spinous process fusion device of FIG. 18 with the expandable wing in a folded position.
Figure 20:
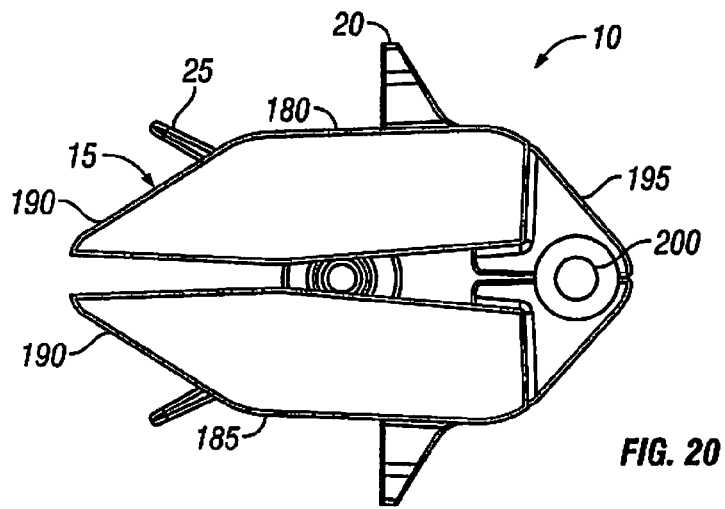
FIG. 20 is a lateral view of an embodiment of the spinous process fusion device of FIG. 19 with the expandable wing in an upright position.

FIGS. 18-20 illustrate another embodiment of the spinous process fusion device 10 having an expandable wing. The embodiment of the spinous process fusion device 10 illustrated in FIGS. 18-20 is similar to the device of FIGS. 12-14, except that the illustrated spinous process fusion device 10 has a thicker body 15. The thicker body 15 should generally provide for distraction of the interspinous space during placement of the device 10. Thus, the device 10 may function as both a spacer and a clamp. As illustrated, the body 15 includes an upper portion 180 and a lower portion 185. Each of the upper portion 180 and a lower portion 185 include a tapered end 190. The tapered end 190 should facilitate insertion of the spinous process fusion device 10 into the interspinous space between adjacent vertebrae. On the opposite side of the body 15 from the tapered end 190, a pivot end 195 is located that connects the upper portion 180 and the lower portion 185. The pivot end 195 may include a pivot axis 200 that permits pivoting of the upper portion 180 and lower portion 185 from a folded position (FIG. 19) to an open position (FIG. 20). The upper portion 180 and lower portion 185 of the body 15 further include a wing opening 205 through which the first wing 20 and the second wing 25 extend. As illustrated, the first wing 20 and/or the second wing 25 may expandable, in that at least one of the wings may expand from a folded position to an upright position. As illustrated, the second wing 25 may expand from a folded position (FIG. 19) to an upright position (FIG. 18). The body 15 may be configured to facilitate folding of the wing(s). By way of example, the body 15 may contain an angled portion 210 to facilitate folding of the second wing 25. As illustrated, the angled portion 210 may be located on a portion of the upper portion 180 that is adjacent the wing opening 205. While not illustrated, a corresponding angled portion and wing opening may be located in the lower portion 185 of the body 15.

Figure 21:
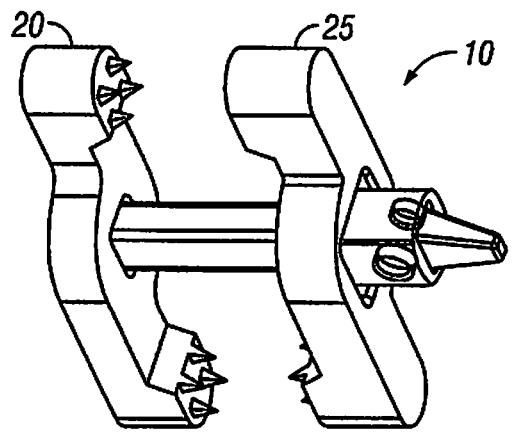
FIG. 21 is a perspective view of another embodiment of a spinous process fusion device of the present invention.
Figure 22:
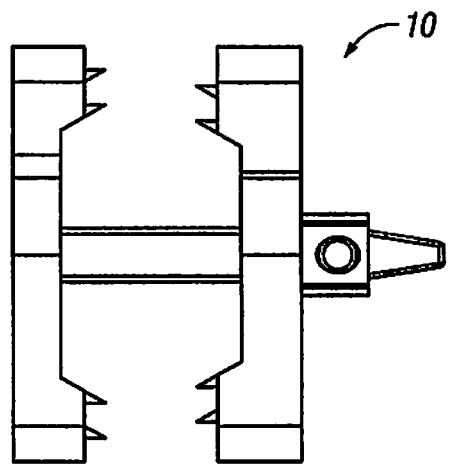
FIG. 22 is a lateral view of an embodiment of the spinous process fusion device of FIG. 21.
Figure 23:
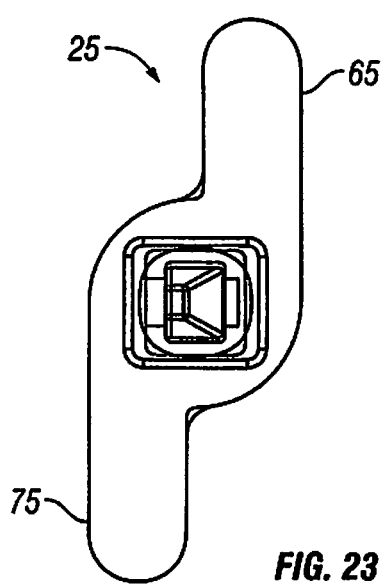
FIG. 23 is a view of a wing for use with an embodiment of a spinous process fusion device of the present invention.
Figure 24:
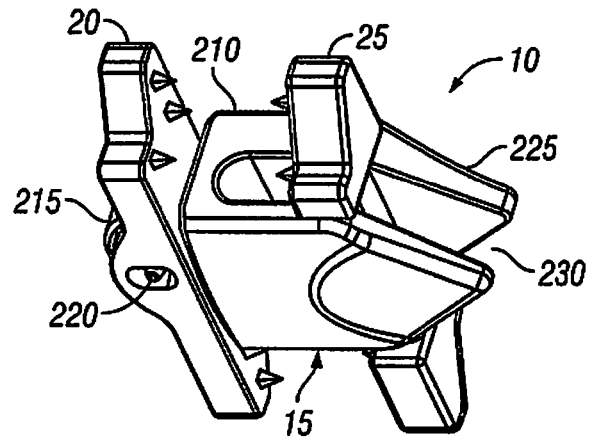
FIG. 24 is a perspective view of an embodiment of a spinous process fusion device of the present invention having a slot for insertion of the second wing.
Figure 25:
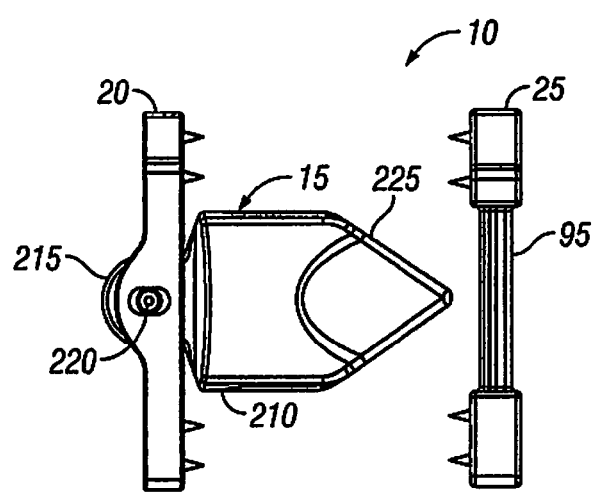
FIG. 25 is a lateral view of an embodiment of the spinous process fusion device of FIG. 24 with the second wing removed.
Figure 26:
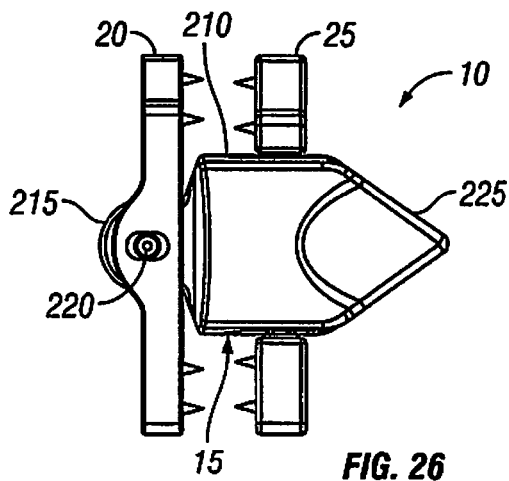
FIG. 26 is a lateral view of an embodiment of the spinous process fusion device of FIG. 24 with the second wing ratcheted in place.
Figure 27:
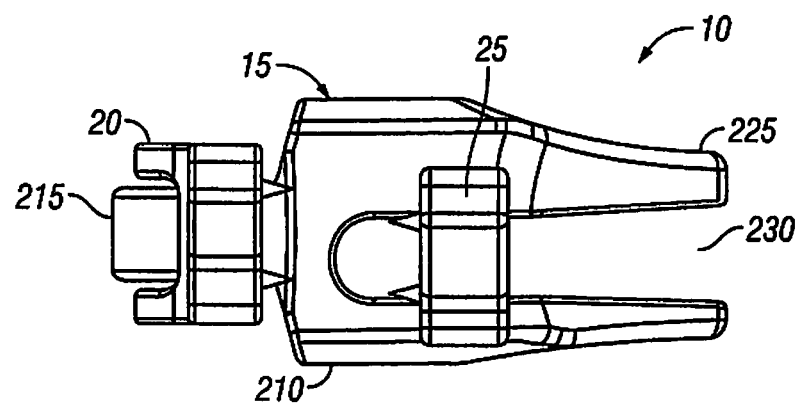
FIG. 27 is a top view of an embodiment of the spinous process fusion device of FIG. 24.

FIGS. 21-23 illustrate another embodiment of the spinous process fusion device 10. As illustrated, the first wing 20 and the second wing 25 may be shaped (for example, with a cutout) to facilitate stacking of more than one spinous process fusion device 10. The second wing 25, for example, may be shaped so that that upper portion 65 and the lower portion 75 will mate. In this manner, an upper portion 65 of the second wing 25 of one spinous process fusion device 10 may contact the same spinous process of the lower portion 65 of the second wing 25 of another spinous process fusion device 10. Once the device 10 is positioned as desired, the second wing 25 may be placed onto the device 10 so that the first wing 20 and the second wing 25 may clamp adjacent spinous processes in place. As previously discussed, the device 10 may include a one-way ratcheting lock, in which the interaction of the protuberances (not shown) with the second wing 25 should prevent removal of the second wing 25. Alternatively, a set screw (not shown) may be used to lock the second wing 25 on the device 10. While not illustrated, the central barrel 135 may be used, for example, to provide for interspinous distraction.

Figure 28:
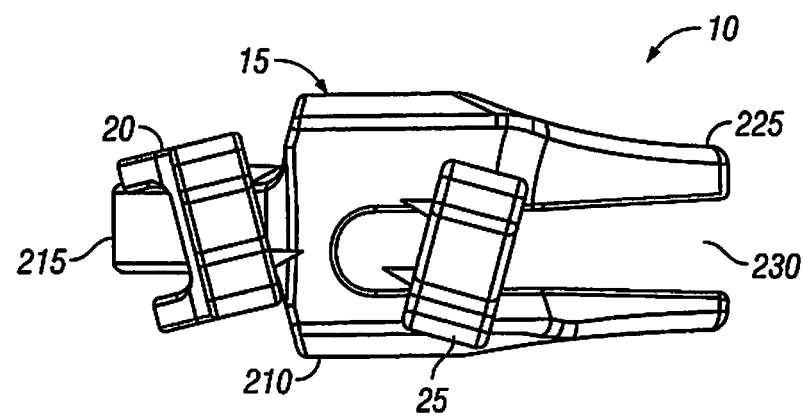
FIG. 28 is a top view of an embodiment of the spinous process fusion device of FIG. 24 with angulation of the wings.

FIGS. 24-28 illustrate another embodiment of the spinous process fusion device 10. As illustrated, the spinous process fusion device 10 may comprise body 15, first wing 20, and second wing 25. In the illustrated embodiment, the body 15 generally may include a central core 210 and a post 215. The post 215 may extend from one end of the central core 210. The first wing 20 may be secured to the post 215 by set screw 220. Alternatively, the first wing 20 may be secured to the post 215 by a one-way ratcheting lock. The central core 210 includes a tapered end 225 and a slot 230. The tapered end 225 should facilitate insertion of the spinous process fusion device 10 into the interspinous space between adjacent vertebrae. Moreover, the width of the central code 210 generally should provide for distraction of the interspinous space during placement of the device 10. Thus, the device 10 may function as both a spacer and a clamp. Once the device 10 is positioned as desired, the second wing 25 may be placed into the slot 230 of the central core 210 so that the first wing 20 and the second wing 25 may clamp adjacent spinous processes in place. As illustrated, the second wing 25, for example, may have the general shape of the bar bell with the central portion 95 having a rod-like shape for insertion into the slot 230. Any of a variety of techniques may be used to secure the second wing 25 in the slot 230. By way of example, a set screw (not shown) or a one-way ratcheting lock may be used for securing the second wing 25. As illustrated in FIG. 28, the first wing 20 and/or the second wing may be configured to angulate on the body 15. By way of example, the first wing 20 and/or the second wing 25 may be configured to rotate about their respective longitudinal axes. A pin (not shown) may be used to facilitate this rotation, in certain embodiments.

FIGS. 29-31 illustrate an embodiment of the spinous process fusion device 10 having clampable wings. As illustrated, the spinous process fusion device 10 includes body 15, first wing 20, and second wing 25. In the illustrated embodiment, the body 15 includes rod 30 onto which the first wing 20 and the second wing 25 may be placed. The first wing 20 and/or the second wing 25, for example, may have the general design of a bear claw. First wing 20 is illustrated in more detail in FIGS. 30-31. As illustrated, the first wing may include an upper flap 235 and a lower flap 240. The upper flap 235 and the lower flap 240 may both comprise teeth 80 for engaging the spinous processes. The upper flap 235 and/or the lower flap 240 may each pivot about rod opening 245. By way of example, the upper flap 235 may pivot from an open position (FIG. 30) to a closed position (FIG. 31). In the closed position, the upper flap 235 and the lower flap 240 may be engaging, for example, opposite sides of a spinous process. Any of a variety of techniques may be used to lock the first wing 20 in the closed position. For example, a set screw (not shown) or a one-way ratcheting lock (not shown) may be used to lock the first wing 20 in the closed position. The second wing 25 may have a similar construction to the first wing 20. In addition, set screws (not shown) may be inserted into a respective screw opening 250 in the first wing 20 and the second wing 25 to lock the wings onto the rod 30. In an alternative embodiment, the device 10 may include a one-way ratcheting lock, in which the interaction of protuberances (not illustrated) with the first wing 20 and/or the second wing 25 should prevent removal of the respective wing.

Figure 32:
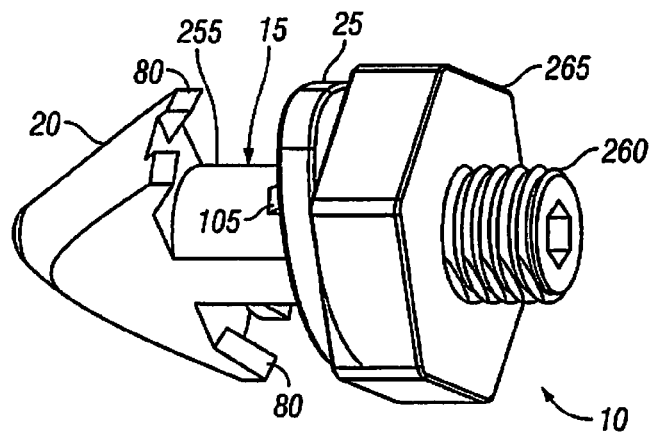
FIG. 32 is a perspective view of an embodiment of a spinous process fusion device of the present invention having a plate in the general shape of an arrowhead.

FIG. 32 illustrates another embodiment of the spinous process fusion device 10. As illustrated, the spinous process fusion device 10 includes body 15, first wing 20, and second wing 25. The body 15 may include rod portion 255 and screw portion 260. In the illustrated embodiment, the first wing 20 is attached to one end of the rod portion 255. The first wing 20, for example, may be in the general shape of an arrowhead. The arrowhead shape should facilitate insertion of the spinous process fusion device 10 between adjacent spinous processes. The first wing 20 further may comprise teeth 80 for engaging the spinous processes. The second wing 25 may be in the general shape of a plate. The second wing 25 may comprise teeth 105 for engaging the spinous processes. Once the device 10 is positioned as desired, the second wing 25 may be placed onto the device 10 over the screw portion 260 of the body 15. Alternatively, the device 10 may be inserted with the second wing 25 in place. A fastener, such as nut 265, may draw together the first wing 20 and the second wing 25 so that the wings may clamp adjacent spinous processes in place. The nut 265 should also secure the second wing 25 on the screw portion 260 of the body 15.

Figure 33:
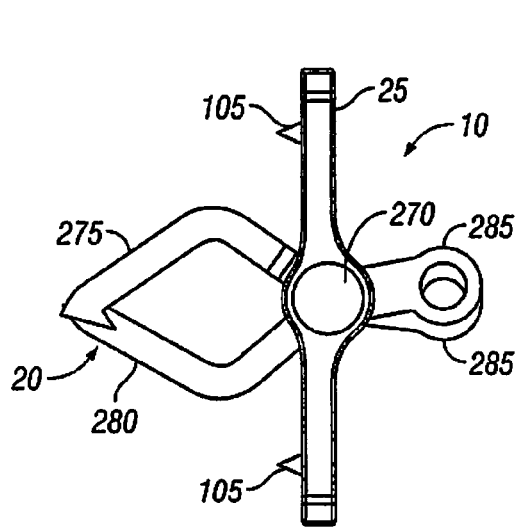
FIGS. 33-34 are lateral views of an embodiment of a spinous process fusion device of the present invention having a pivoting scissor-type clamp.
Figure 34:
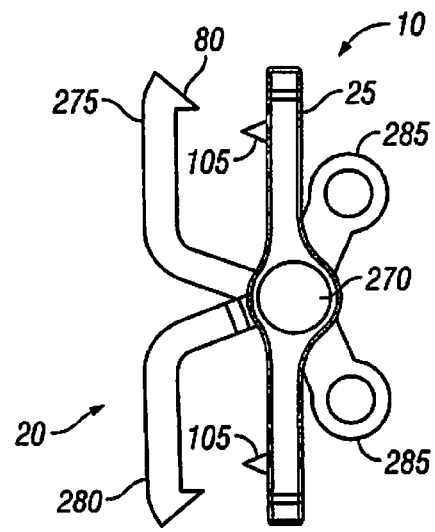

FIGS. 33-34 illustrate an embodiment of the spinous process fusion device 10 having a pivoting scissor-type clamp. As illustrated, the spinous process fusion device 10 includes first wing 20, second wing 25, and set screw 270. The set screw 270 generally may connect the first wing 20 and the second wing 25. The second wing 25 may be in the generally shape of a plate with an opening for insertion of the set screw 270. In the illustrated embodiment, the first wing 20 is in the general shape of a clamp jaw having a top jaw portion 275 and a bottom jaw portion 280. Each of the top jaw portion 275 and the bottom jaw portion 280 contain teeth 80 for engaging the spinous processes. Additionally, each of the top jaw portion 275 and the bottom jaw portion 280 has a handle 285. The top jaw portion 275 and the bottom jaw portion 280 are connected at the set screw 270 such that the set screw acts as a pivot for both the top jaw portion 275 and the bottom jaw portion 280. By way of example, the top jaw portion 275 and the bottom jaw portion 280 may pivot from an initial position (FIG. 33) to an engaged position (FIG. 34). As illustrated by FIG. 33, the top jaw portion 275 and the bottom jaw portion 280 are both bent so that in the initial position the first wing 20 has an angled end that facilitates insertion of the device 10 between adjacent spinous processes. Once the device 10 has been inserted between adjacent spinous processes, the handle 285 of each the top jaw portion 275 and the bottom jaw portion 280 may be used to pivot the first wing 20 to the engaged position such that the teeth 80 of the first wing 20 engage the adjacent spinous processes both above and below the interspinous space. In the engaged position, the teeth 105 of the second wing 25 should also engage the adjacent spinous processes both above and below the interspinous space. Once the first wing 20 has been pivoted to the engaged position, the screw 270 may be used to lock the device 10 in position. By way of example, the device 10 generally can be locked in a position in which the first wing 20 and the second wing 25 clamp the spinous processes in place.

FIGS. 35-36 illustrate another embodiment of the spinous process fusion device 10 having a pivoting plate. As illustrated, the spinous process fusion device 10 includes body 15, first wing 20, and second wing 25. In the illustrated embodiment, the second wing 25 includes two wings, shown on FIGS. 35-36 as upper wing 290 and lower wing 295. As illustrated, the upper wing 290 and the lower wing 295 both may include a tapered end. Each of the upper wing 290 and the lower wing 295 include teeth 80. While not illustrated, the first wing 20 may also include teeth. In the illustrated embodiment, the upper wing 290 and the lower wing 295 are pivotably connected to the body 15 at pivot connection 300. By way of example, the upper wing 290 and the lower wing 295 may pivot from an initial position (FIG. 35) to an engaged position (FIG. 36). As illustrated, the upper wing 290 and the lower wing 295 may form a rounded end 305 when the device 10 is in the initial position. The rounded end 305 may, for example, facilitate insertion of the device 10 between adjacent spinous processes. Once the device 10 has been inserted between adjacent spinous processes, the second wing 25 may be moved along the body 15 resulting in pivoting of the upper wing 290 and the lower wing 295 to the engaged position. As illustrated, the body 15 includes a spreader 310 that extends from the second wing 25. The second wing 25 may drive spreader 310 between the tapered ends of the upper wing 290 and the lower wing 295 forcing the wings to pivot to the engaged position. In the engaged position, the teeth 80 on the upper wing 290 and the lower wing 295 may engage the adjacent spinous processes both above and below the interspinous space. In the engaged position, the teeth (if present) on the second wing 25 may also engage the adjacent spinous processes both above and below the interspinous space. In this manner, the first wing 20 and the second wing 25 may clamp adjacent spinous processes in place. As previously discussed, the device 10 may include a one-way ratcheting lock, in which the interaction of protuberances with the second wing 25 should prevent removal of the second wing 25.

Figure 39:
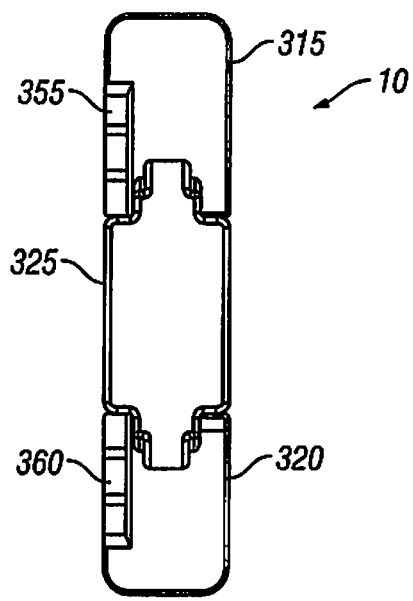
FIG. 39 is an end view of an embodiment of the spinous process fusion device of FIG. 38.

FIGS. 37-39 illustrate an embodiment of the spinous process fusion device 10 having parallel distraction plates. As illustrated, the spinous process fusion device 10 includes a top distraction element 315, a bottom distraction element 320, and a plate 325. In certain embodiment, the top distraction element 315 and the bottom distraction element 320 may be bent. For example, the top distraction element 315 and the bottom distraction element 320 may be generally 1-shaped. As illustrated, the top distraction element 315 includes a base arm 330 and an extended arm 335. As illustrated, the extended arm 335 may extend transversely and outwardly from one end of the base arm 330, for example, with the base arm 330 and the extended arm 335 generally forming a 90° angle. The bottom distraction element 320 also includes a base arm 340 and an extended arm 345. As illustrated, the extended arm 345 may extend outwardly and transversely from one end of the base arm 340, for example, with the base arm 340 and the extended arm 345 generally forming a 90° angle. While not illustrated, the extended arms 335, 345 may contain teeth for engaging spinous processes. The teeth may extend from the extended arms 335, 345 on the same side as the base arms 330, 340. In addition, the base arms 330, 340 may each have a tapered end so that when the device 10 is in an initial position (FIG. 37) the top distraction element 315 and the bottom distraction element 320 form a tapered end 350. The tapered end 350 may facilitate insertion of the device 10 between adjacent spinous processes. When the device 10 is in the initial position (FIG. 37), it may be inserted between adjacent processes. Once the device 10 has been inserted between adjacent spinous processes, the handle portions 355, 360 of the extended arms 335, 345 may be used to spread the top distraction element 315 and the bottom distraction element 320, resulting in movement of the device 10 to the engaged position (FIG. 38) and distraction of the interspinous space. The plate 325 may then be placed over the tapered ends of the base arms 330, 335 to clamp the adjacent spinous processes in place. The plate 325 generally should have openings 365, 370 for receiving the base arms 330, 335. Any of a variety of suitable techniques may then be used to lock the device 10 in place. By way of example, set screws may be used to lock in the base arms 330, 335 in the openings 365, 370 of the plate 325.

Figure 40:
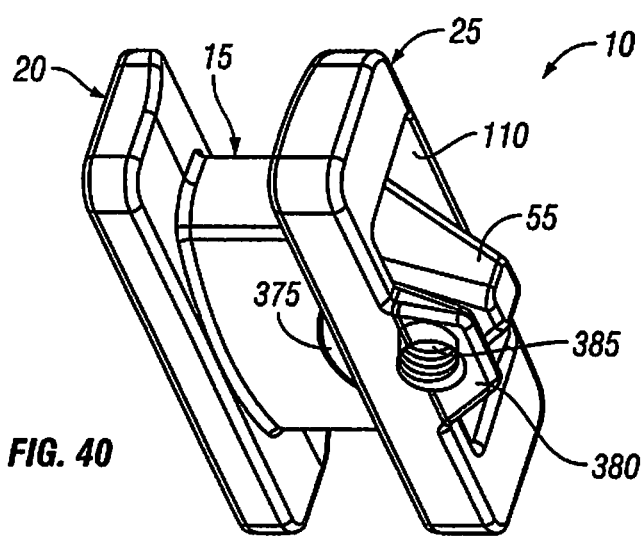
FIG. 40 is a perspective view of another embodiment of the spinous process fusion device of the present invention.

FIG. 40 illustrates another embodiment of the spinous process fusion device 10. As illustrated, the spinous process fusion device 10 includes body 15, first wing 20, and second wing 25. The body 15 may include a tapered end 55 and a slot 375 formed in the body. The tapered end 55 may, for example, facilitate insertion of the device 10 between adjacent spinous processes. While not illustrated, the first wing 20 and the second wing 25 may include teeth for engaging spinous processes. The first wing 20 may be attached at the opposite end of the body 15 from the tapered end 55. The second wing 25 may include an opening 110 that may allow placement of the second wing 25 onto the body 15. The second wing 25 also may include a tab portion 380 that is disposed generally in the middle portion of the second wing 25. The tab portion 380 may include an opening 385 for receiving a set screw. To lock the second wing 25 on the body 15, the set screw may be inserted through the opening 110 and the slot 375. Accordingly, the second wing 25 may be locked on the body 15 at any position along the slot 375. Screwing at an angle may generally result in angulation of second wing 25.

Figure 41:
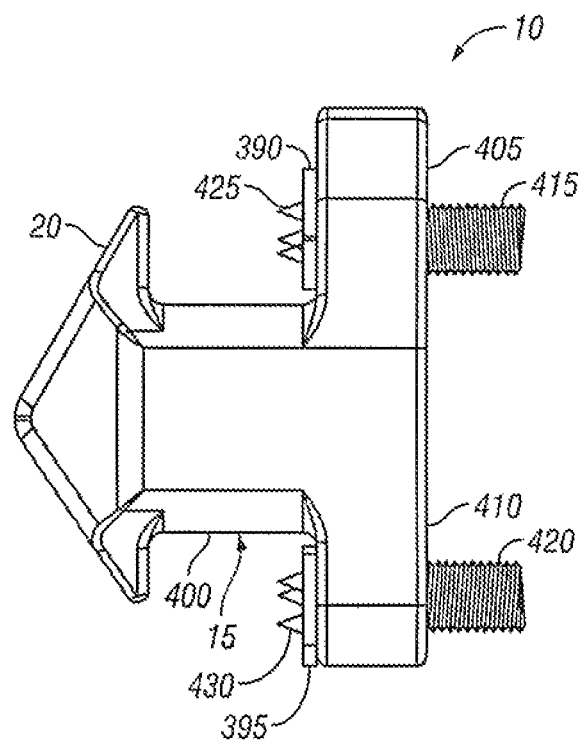
FIGS. 41-42 are lateral view of another embodiment of the spinous process fusion device of the present invention having a plate in the general shape of an arrowhead.
Figure 42:
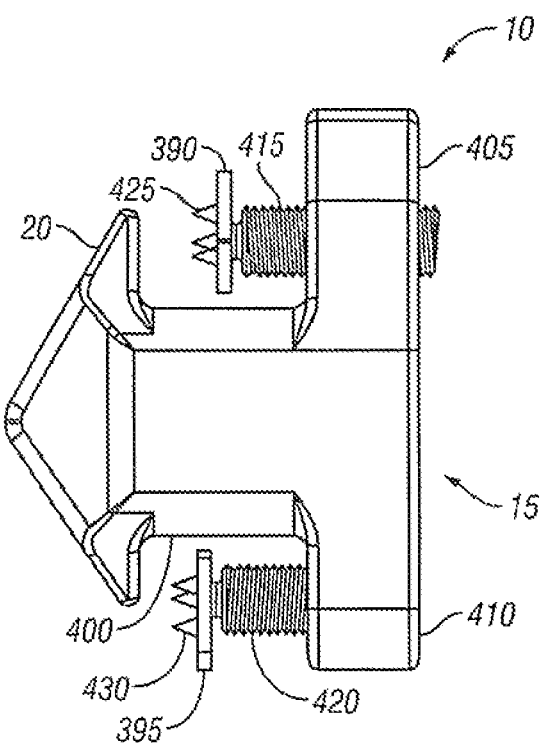

FIGS. 41-42 illustrate another embodiment of a spinous process fusion device 10 of the present invention. As illustrated, the spinous process fusion device 10 includes body 15, first wing 20, top plate 390, and bottom plate 395. The body 15 may be generally t-shaped and have a base portion 400 and two extended portions 405, 410 that extend transversally and outwardly from opposite sides of one end of the base portion 400. Each of the extended portions 405, 410 may include an opening for receiving an elongated member. In certain embodiments, the opening may be threaded. The first wing 20 maybe attached to the base portion 400 at the opposite end of the base portion 400 from the extended portions 405, 410. The first wing 20, for example, may be in the general shape of an arrowhead. The arrowhead shape of the first wing 20 should facilitate insertion of the spinous process fusion device 10 between adjacent spinous processes. While not illustrated, the first wing 20 further may comprise teeth for engaging the spinous processes. The top plate 390 and the bottom plate 395 may be coupled to respective elongated members, such as screws 415, 420. In certain embodiments, the top plate 390 and the bottom plate 395 may be configured to angulate on their respective screw. The top plate 390 and the bottom plate 395 may include teeth 425, 430 for engaging spinous processes. In the illustrated embodiment, when the screws 415, 420 are turned the plates 390, 395 should travel towards the first plate 20. When the screws 415, 420 are turned in the opposite direction, the plates 390, 395 should travel away from the first plate 20. To clamp adjacent spinous processes in place, the screws 415, 420 may be turned until a spinous process is engaged between first wing 20 and top plate 390, and an adjacent spinous process is engaged between first wing 20 and bottom plate 395.

Figure 43:
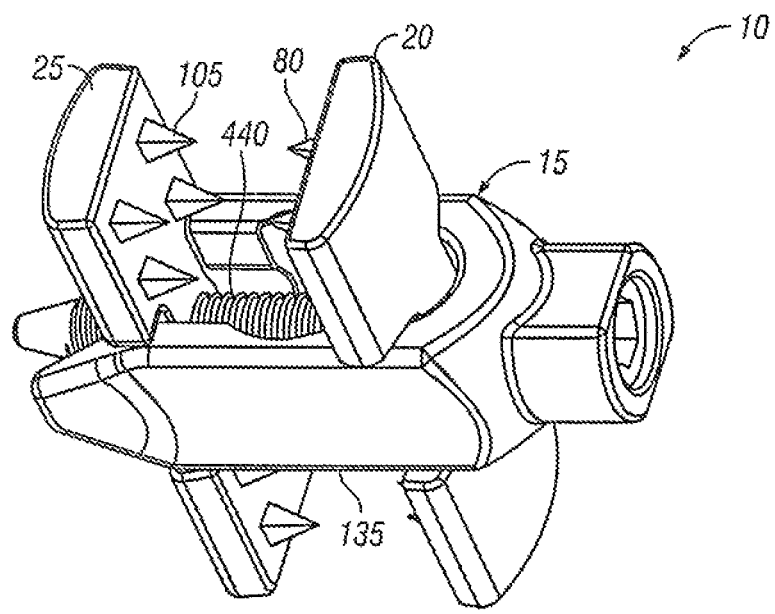
FIG. 43 is a perspective view of an embodiment of a spinous process fusion device of the present invention having a central bolt for drawing the first and second wings together.
Figure 44:
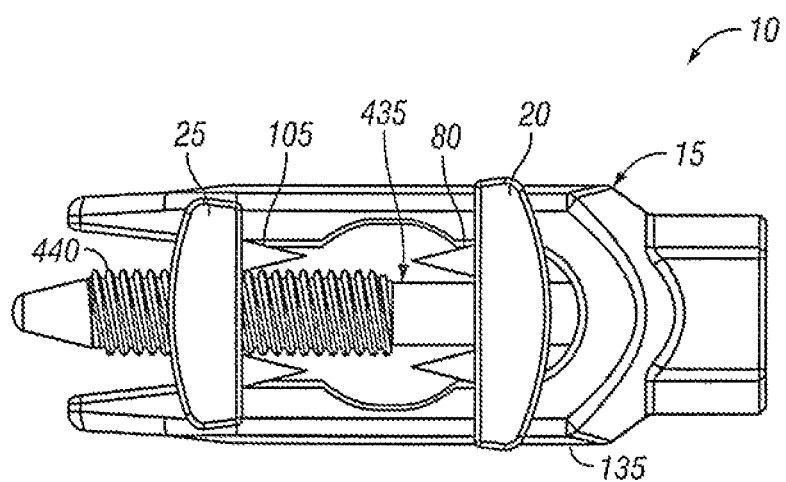
FIG. 44 is a top view of an embodiment of the spinous process fusion device of FIG. 43.

FIGS. 43-44 illustrate another embodiment of a spinous process fusion device 10 of the present invention comprising a bolt 435 having a threaded portion 440. As illustrated, the spinous process fusion device 10 comprises body 15, first wing 20, and second wing 25. In the illustrated embodiment, the body includes central barrel 135 and bolt 435. As previously discussed, the central barrel 135 generally may have a width sufficient for distraction of the interspinous space. The first wing 20 may comprise teeth 80, and the second wing 25 may also comprise teeth 105. Rotation of the bolt 435 should result in the first wing 20 and the second wing 25 being drawn together. By way of example, the second wing 25 should move along the threaded portion 440 when the bolt 435 is rotated. Rotation of the bolt 435 in the opposite direction should result in movement of the first wing 20 and the second wing 25 in the opposite direction. In operation, the second wing 25 may be placed onto the device and the bolt 435 such that the first wing 20 and the second wing 25 are drawn together clamping adjacent spinous processes in place.

It should be understood that a variety of different techniques may be used in accordance with embodiments of the present invention to secure a wing (e.g., second wing 25) onto the body 15. By way of example, FIGS. 1-2 illustrate an embodiment in which a one-way ratcheting lock prevents removal of second wing 25 from the body 15. Other suitable techniques for locking the second wing 25 may include use of a spreader-type lock, a camlock, a set screw, a threaded rod, or any of a variety of other techniques some of which are described above.

Figure 45:
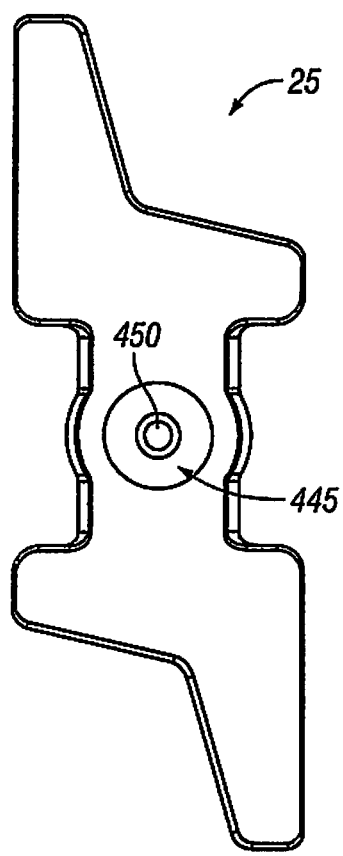
FIGS. 45-47 illustrate an embodiment of a spinous process fusion device of the present invention that includes a cam-lock.
Figure 46:
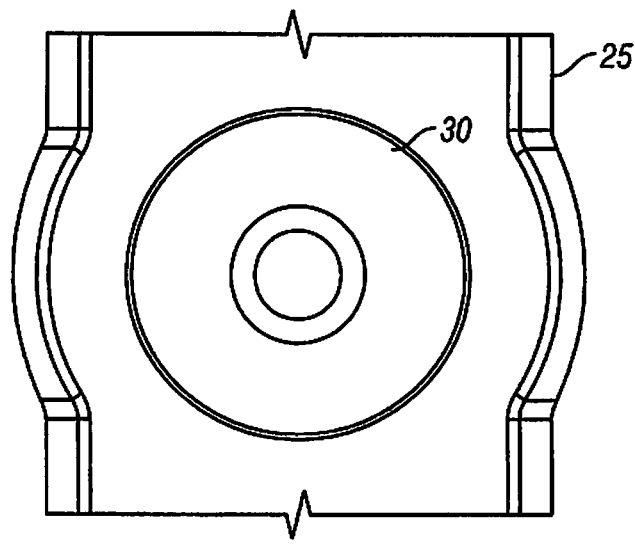
Figure 47:
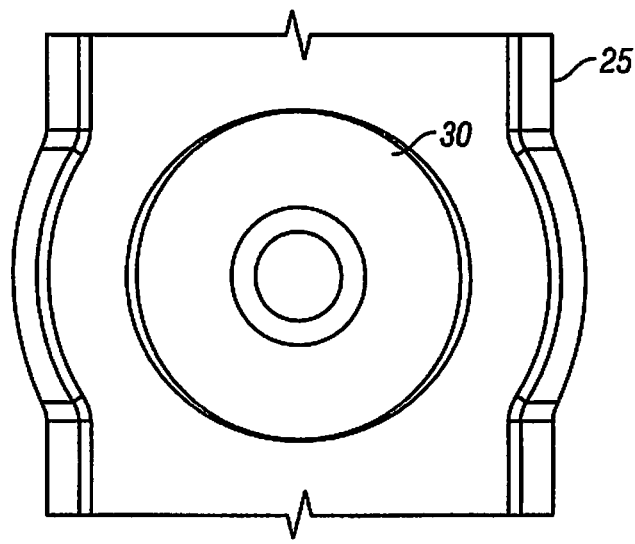
Figure 48:
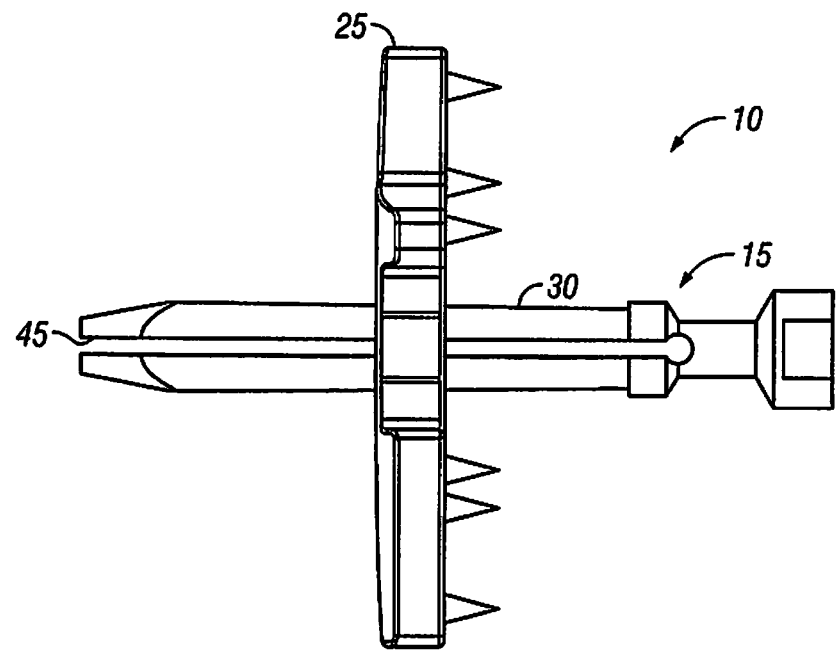
FIGS. 48-51 illustrate an embodiment of a spinous process fusion device of the present invention that includes a spreader-type lock.
Figure 49:
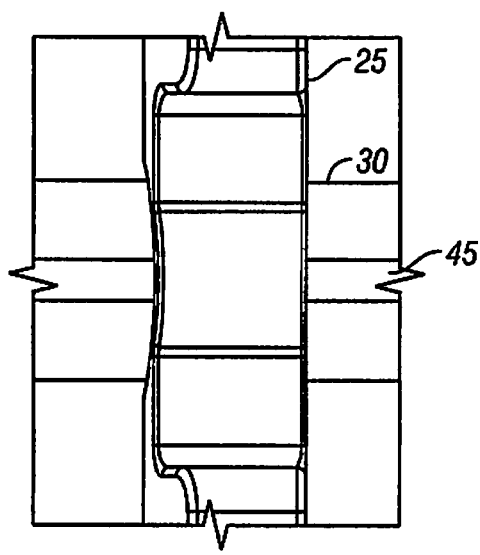

FIGS. 45-47 illustrate an embodiment of the present invention that includes a camlock for securing a wing (e.g., second wing 25). As illustrated, the second wing 25 generally may be placed over rod 30. The rod 30 generally may be configured such that the second wing 25 may be secured on the rod 30 by a camlock mechanism. With the camlock mechanism, axial rotation of the rod 30 should result in securing of the second wing 25 onto the body 15. FIG. 46 illustrates the camlock in an initial position. FIG. 47 illustrates the camlock in a locked position. Those of ordinary skill in the art will appreciate that a camlock assembly may also be incorporated into embodiments of the present invention that include a one-way ratcheting lock. By way of example, the camlock may be used to facilitate engagement of ratcheting members on the second wing 25 with protuberances of the rod 30.

Figure 50:
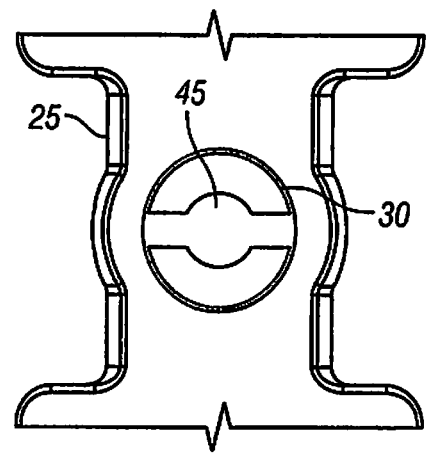
Figure 51:
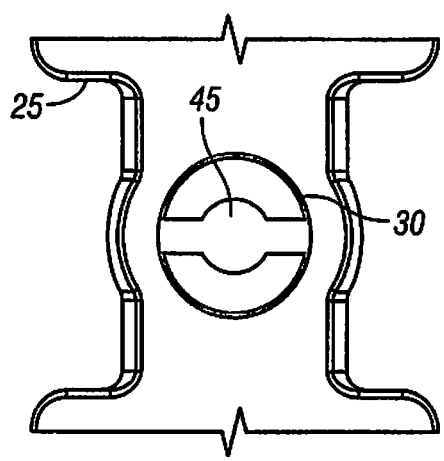

FIGS. 48-51 illustrate an embodiment of the present invention that includes a spreader-type lock for securing a wing (e.g., second wing 25). As illustrated, the spinous process fusion device 10 may include a body 15 and a second wing 25. For purposes of this illustration, the first wing 20 is not shown. However, the first wing 20 generally should be present during operation of the device 10, in accordance with embodiments of the present invention. In the illustrated embodiment, the second wing 25 generally includes a rod 30 that may be generally configured to spread to increase the diameter of the rod 30. In the illustrated embodiment, the rod 30 generally may include an opening 45 extending there through in the direction of pits longitudinal axis. The rod 30 may be configured so that insertion of the pin 50 or a screw spreads the rod 30. In this manner, the diameter of the rod 30 may be increased. The diameter of the rod 30 prior to insertion of the pin 50 generally should allow for movement of the second wing 25 over the rod. However, once the pin 50 has been inserted, the rod 30 should spread, securing the second wing 25 onto the body 15. FIG. 50 illustrates the spreader-type lock in the initial position. FIG. 51 illustrates the spreader-type lock in the locked position. As previously described, the spreader-type lock may be incorporated into embodiments of the present invention that include a one-way ratcheting lock.

The spinous process fusion device 10 may comprise, for example, any of a variety of biocompatible materials, including metals, ceramic materials, and polymers. Examples of biocompatible materials include titanium, stainless steel, aluminum, cobalt-chromium, alloys, and polyethylene. By way of example, one or more components (e.g., central barrel 25, central core 210, etc.) of the device 10 may comprise polyetheretherketone.

Additional Embodiments

FIGS. 52-57 illustrate different views of an alternative embodiment of a spinous process fusion device of the present invention that includes arced or curved first and second wings. While the curved first and second wings can be suitable for vertebral bodies at any level of the spine, the curved first and second wings are of particular benefit for accommodating the curved features of the sacroiliac S1 anatomy.

The spinous process fusion device 10 includes many similar features as those devices described above, including a body comprising a rod 30 having protuberances 60 for providing a ratcheting mechanism, a central barrel 135 having a self-distracting tapered end 150, and first and second wings 520 and 525 having protruding teeth 80 and 105 configured to engage a spinous process of a vertebral body. The wings 520 and 525 can be placed and adjusted relative to the rod 30 and central barrel 135 similarly to the wings of the devices described above. In contrast, however, the first wing 520 and second wing 525 of the device 10 are prominently curved and sweeped to accommodate a curved vertebral body, such as the S1 anatomy, as discussed further below.

Figure 52:
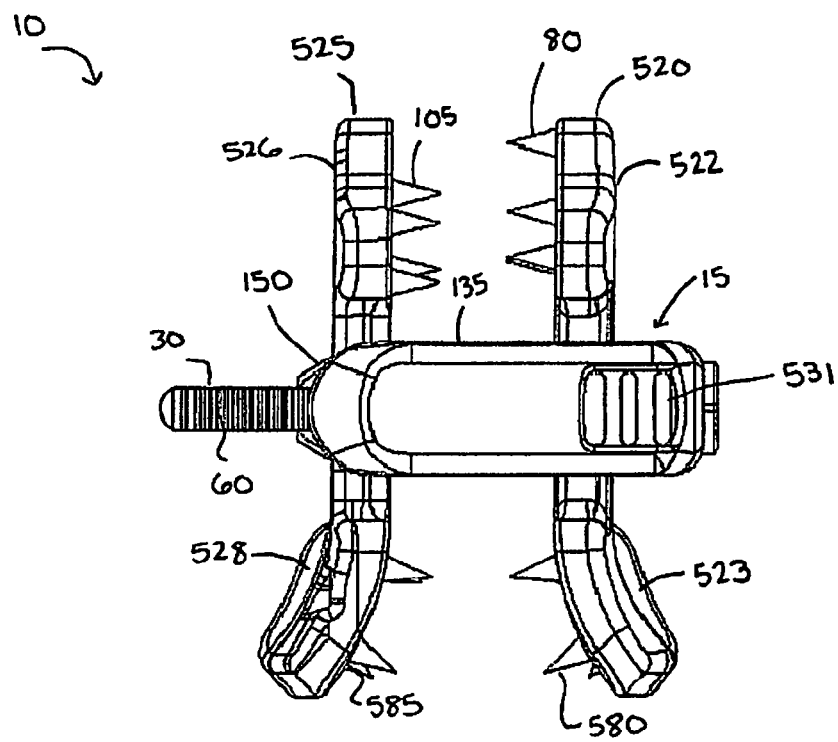
FIGS. 52-59 illustrate different views of alternative embodiments of a spinous process fusion device of the present invention that includes curved first and second wings.

In some embodiments, both the first wing 520 and second wing 525 are curved and sweeped. As shown in FIG. 52, the first wing 520 includes a first substantially straight portion 522 that transitions into a second substantially curved portion 523. The first substantially straight portion 522 includes teeth 80 that can engage a spinous process, while the second substantially curved portion 523 includes teeth 580 formed along a curved surface that can engage the sacroiliac. Likewise, the second wing 525 includes a first substantially straight portion 526 that transitions into a second substantially curved portion 528. The first substantially straight portion 526 includes teeth 105 that can engage the opposite side of a spinous process, while the second substantially curved portion 523 includes teeth 585 formed along a curved surface that can also engage the sacroiliac. In some embodiments, the teeth 80, 105 used to engage the spinous process are the same or similar (e.g., in height and geometry) to the teeth 580, 585 used to engage the sacroiliac, while in other embodiments, differently configured teeth can be provided.

In some embodiments, the curved portions of the first and second wings 520 and 525 include a sweep that matches the average sacral inclination and breadth for humans in order to provide optimal grip and coverage. In some embodiments, the curved portions can have a curvature relative to the straight portions of between about 0 and 90 degrees. While in some embodiments, the curvature of the first wing is substantially similar to the curvature of the second wing, in other embodiments, the curvature is different to accommodate the unique anatomy of individual patients.

As shown in FIG. 52, the first substantially straight portion and the second substantially curved portion of each of the wings can be formed monolithically. In other embodiments, the curved portion is formed separately and is attached to the straight portion.

In some embodiments, the curvature of the substantially curved portion 523, 528 is fixed relative to the substantially straight portion 522, 526 for each of the wings 520 and 525. In other embodiments, the substantially curved portions 523 and 528 are adjustable and/or polyaxial. For example, the curved portions 523 and 528 can include a mechanical hinge feature that allows the angle of curvature of the curved portions to be modified. In some embodiments, a bendable material, such as an elastomer, can be provided between the straight and curved portions to facilitate bending of the curved portions of the wings.

The wings 520 and 525 can have a fixed height, such as between about 15 and 90 mm, or between about 25 and 75 mm. In other embodiments, the wings 520 and 525 can have an adjustable height, thereby helping to accommodate the characteristics of individual patients.

Figure 53:
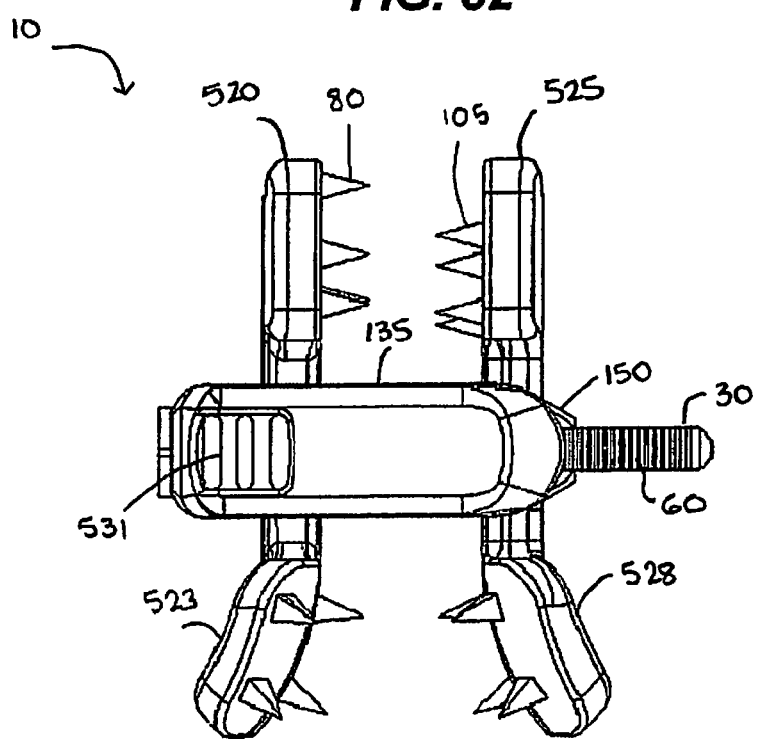
Figure 54:
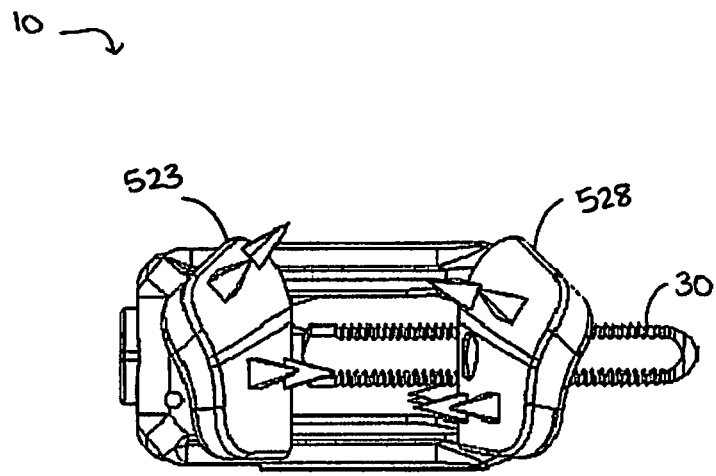
Figure 55:
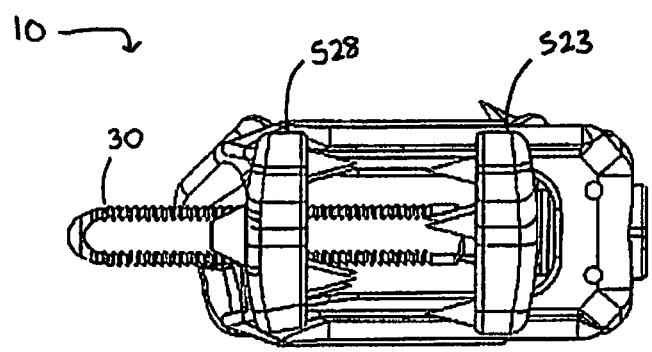
Figure 56:
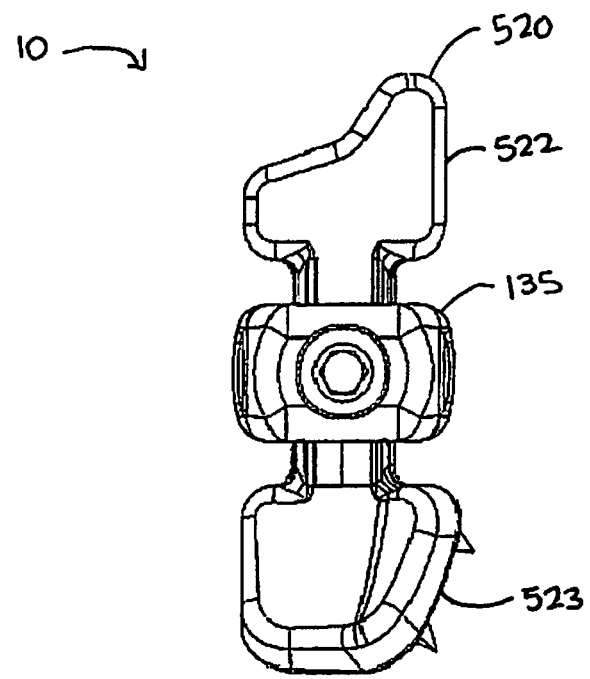
Figure 57:
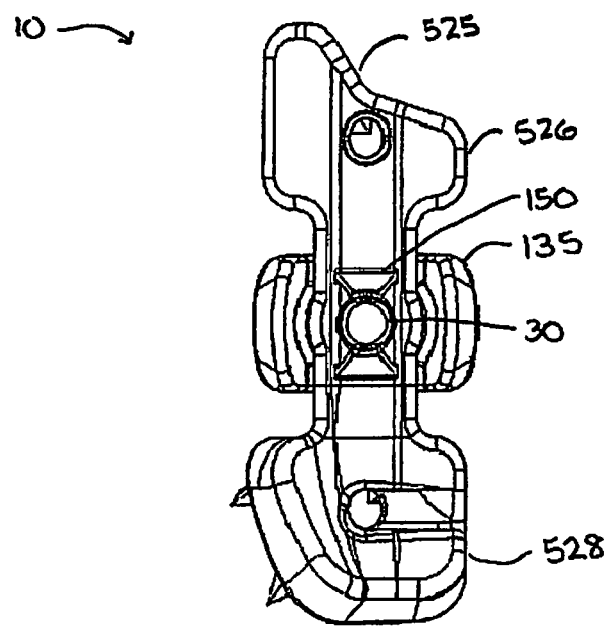

In addition to the features discussed above, the central barrel 135 of the fusion device 10 can include a side slot or pocket 531 (as shown in FIGS. 52 and 53) for easy grasping by an insertion instrument. In some embodiments, a side slot is formed on both sides of the body of the central barrel 135. By providing such slots, the fusion device 10 can advantageously be delivered to a desired location within the body with ease. In other embodiments, the insertion slots can be placed on a top and/or bottom surface of the central barrel 135.

Figure 58:
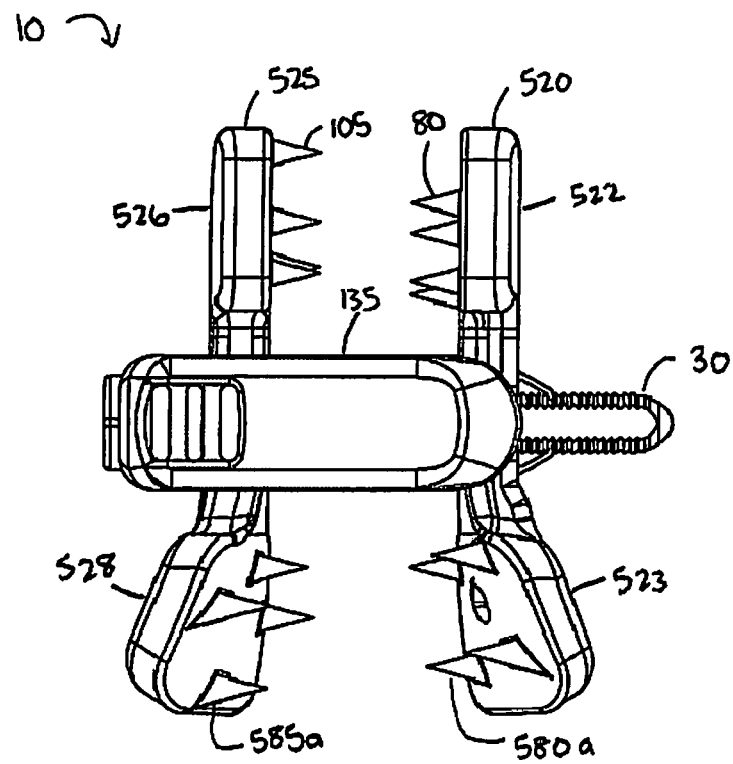
Figure 59:
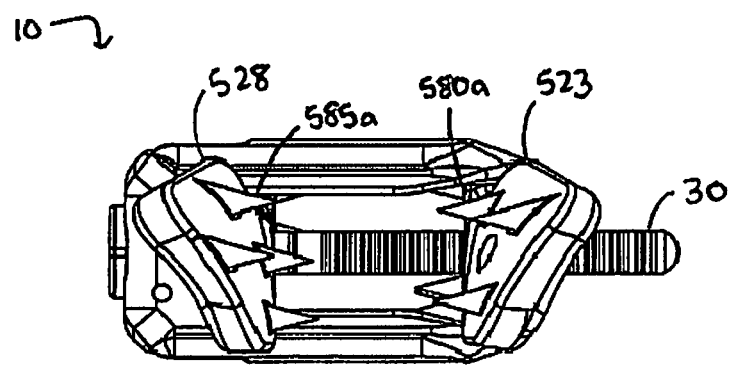

FIGS. 58 and 59 show front and bottom views, respectively, of an alternative embodiment of a spinous process fusion device. Like the device in FIG. 52, the fusion device 10 in FIGS. 58 and 59 includes a rod 30 for providing a ratcheting mechanism, a central barrel 135 having a self-distracting tapered end, and first and second wings 520 and 525.

As in the previous embodiments, both the first wing 520 and second wing 525 are curved and swept. The first wing 520 includes a first substantially straight portion 522 that transitions into a second substantially curved portion 523, while the second wing 525 includes a first substantially straight portion 526 that transitions into a second substantially curved portion 528. The first wing 520 and second wing 525 include teeth 80 and 105 for engagement to a spinous process along their substantially straight portions as in prior embodiments. However, along the curved portions 523 and 528, the teeth 580a and 585a have a modified geometry. The teeth 580a and 585a are oriented to face the same inward direction as the teeth 80 and 105. The teeth 580a, 585a thus advantageously face inward toward the spine, thereby advantageously accommodating the anatomy of the spine. By facing the spine, the teeth also advantageously allow lateral compression from a regular compressor. In addition, the teeth do not drag across the sacrum as the implant is compressed. In some embodiments, the teeth are cut with desirable angles across each face and have kite-shaped bases, where the teeth intersect the curve. In some embodiments, the teeth can also be cut with different angles across each face, so that the base is a perfect square.

The first substantially straight portion 522 includes teeth 80 that can engage a spinous process, while the second substantially curved portion 523 includes teeth 580 formed along a curved surface that can engage the sacroiliac.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. An implantable device, comprising:
a body comprising a rod member and a central barrel having first and second sides for distracting an interspinous space;
a first wing operatively attached to the body, the first wing comprising a substantially straight portion that transitions into a substantially curved portion having a curved surface configured to engage a sacroiliac anatomy, wherein the curvature of the substantially curved portion is fixed relative to the substantially straight portion; and
a second wing operatively attached to the body, the second wing comprising a substantially straight portion that transitions into a substantially curved portion having a curved surface configured to engage the sacroiliac anatomy, wherein the curvature of the substantially curved portion is fixed relative to the substantially straight portion,
wherein the first and second sides of the central barrel extend over and around the first and second wings,
wherein a first longitudinal axis extends along the first wing and a second longitudinal axis extends along the second wing, wherein the curved surface of the substantially curved portion of the first wing curves outwardly relative to the first longitudinal axis and the curved surface of the substantially curved portion of the second wing curves outwardly relative to the second longitudinal axis such that a distance of separation between the substantially curved portion of the first wing and the substantially curved portion of the second wing is greater than a distance of separation between the substantially straight portion of the first wing and the substantially straight portion of the second wing,
wherein the rod member comprises a plurality of protuberances which are configured to mate with a ratcheting member to create a one-way ratcheting lock to prevent removal of at least one of the first and second wings.

2. The device of claim 1, wherein the first wing includes a plurality of teeth formed on the substantially straight portion.

3. The device of claim 2, wherein the first wing includes a plurality of teeth formed on the curved surface of the substantially curved portion.

4. The device of claim 1, wherein a degree of curvature of the first wing is substantially the same as the curvature of the second wing.

5. The device of claim 1, wherein a degree of curvature of the substantially curved portion relative to the substantially straight portion of the first wing is between 0 and 90 degrees.

6. The device of claim 1, wherein the rod member has a tapered end, and wherein the plurality of protuberances on the rod member are in the shape of inclined wedges having inclined portions extending in the direction of the tapered end of the rod member.

7. The device of claim 1, wherein the plurality of protuberances are arranged on a first side and a second side of the rod member.

8. The device of claim 1, wherein a distance of separation between a distal-most end of the curved portion of the first wing and a distal-most end of the curved portion of the second wing is greater than a distance of separation between the remaining curved portions of the first and second wings.

9. The device of claim 1, wherein the body extends from a first end to a second end, and the first and second wings are attached to the body such that the first and second ends of the body extend beyond the first and second wings.

10. An implantable device, comprising:
a body comprising a rod member and a central barrel having first and second sides for distracting an interspinous space;
a first wing operatively attached to the body, the first wing comprising a substantially straight portion and a substantially curved portion having a curved surface including a first set of teeth and configured to engage a sacroiliac anatomy; and
a second wing operatively attached to the body, the second wing comprising a substantially straight portion and a substantially curved portion having a curved surface including a second set of teeth and configured to engage a sacroiliac anatomy,
wherein the first and second sides of the central barrel extend over and around the first and second wings,
wherein a first longitudinal axis extends along the first wing and a second longitudinal axis extends along the second wing, wherein the curved surface of the substantially curved portion of the first wing curves outwardly relative to the first longitudinal axis and the curved surface of the substantially curved portion of the second wing curves outwardly relative to the second longitudinal axis such that a distance of separation between the substantially curved portion of the first wing and the substantially curved portion of the second wing is greater than a distance of separation between the substantially straight portion of the first wing and the substantially straight portion of the second wing,
wherein the rod member comprises a plurality of protuberances which are configured to mate with a ratcheting member to create a one-way ratcheting lock to prevent removal of at least one of the first and second wings.

11. The device of claim 10, wherein the first wing includes a substantially straight portion that transitions into the substantially curved portion.

12. The device of claim 11, wherein the substantially straight portion includes a set of teeth.

13. The device of claim 12, wherein the set of teeth on the substantially straight portion have a different height and/or geometry from the set of teeth on the substantially curved portion.

14. The device of claim 10, wherein the first wing has a curvature of between about 0 and 90 degrees.

15. An implantable device, comprising:
a body comprising a central barrel having first and second sides for distracting an interspinous space and a rod member;
a first wing operably attached to the body, the first wing comprising a substantially straight portion that transitions into a substantially curved portion having a curved surface configured to engage a sacroiliac anatomy, wherein the curvature of the substantially curved portion is fixed relative to the substantially straight portion; and
a second wing operably attached to the body, the second wing comprising a substantially straight portion that transitions into a substantially curved portion having a curved surface configured to engage a sacroiliac anatomy, wherein the curvature of the substantially curved portion is fixed relative to the substantially straight portion,
wherein the first and second sides of the central barrel extend over and around the first and second wings,
wherein a first longitudinal axis extends along the first wing and a second longitudinal axis extends along the second wing, wherein the curved surface of the substantially curved portion of the first wing curves outwardly relative to the first longitudinal axis and the curved surface of the substantially curved portion of the second wing curves outwardly relative to the second longitudinal axis such that a distance of separation between the substantially curved portion of the first wing and the substantially curved portion of the second wing is greater than a distance of separation between the substantially straight portion of the first wing and the substantially straight portion of the second wing,
wherein the rod member comprises a plurality of protuberances which are configured to mate with a ratcheting member to create a one-way ratcheting lock to prevent removal of at least one of the first and second wings.

16. The device of claim 15, wherein the substantially straight portion of the first wing includes a first set of teeth.

17. The device of claim 16, wherein the substantially curved portion of the first wing includes a second set of teeth.

18. The device of claim 17, wherein the first set of teeth have a different shape and/or geometry from the second set of teeth.

19. The device of claim 15, wherein the substantially curved portion of the first wing has a different degree of curvature from the substantially curved portion of the second wing.

20. The device of claim 15, wherein the substantially straight portion and the substantially curved portion of the first wing are formed monolithically.

* * * * *